(12) United States Patent
Huisman et al.

(10) Patent No.: US 10,045,987 B2
(45) Date of Patent: Aug. 14, 2018

(54) IMIDAZOYL ANILIDE DERIVATIVES AND METHODS OF USE

(71) Applicant: Codexis, Inc., Redwood City, CA (US)

(72) Inventors: Gjalt W. Huisman, Redwood City, CA (US); Jed Lee Hubbs, Thalwil (CH); Xiyun Zhang, Fremont, CA (US); Robert Osborne, Raleigh, NC (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 15/504,134

(22) PCT Filed: Aug. 27, 2015

(86) PCT No.: PCT/US2015/047146
§ 371 (c)(1),
(2) Date: Feb. 15, 2017

(87) PCT Pub. No.: WO2016/033304
PCT Pub. Date: Mar. 3, 2016

(65) Prior Publication Data
US 2017/0273978 A1    Sep. 28, 2017

Related U.S. Application Data

(60) Provisional application No. 62/043,083, filed on Aug. 28, 2014, provisional application No. 62/043,278, filed on Aug. 28, 2014.

(51) Int. Cl.
*A61K 31/506*   (2006.01)
*C07D 401/14*   (2006.01)
*C07D 239/22*   (2006.01)
*C07D 233/54*   (2006.01)
*C07C 59/185*   (2006.01)

(52) U.S. Cl.
CPC .......... *A61K 31/506* (2013.01); *C07C 59/185* (2013.01); *C07D 233/54* (2013.01); *C07D 239/22* (2013.01); *C07D 401/14* (2013.01)

(58) Field of Classification Search
CPC .. C07D 233/54; C07D 239/22; C07D 401/14; C07C 59/185; A61K 31/506
See application file for complete search history.

(56) References Cited

U.S. PATENT DOCUMENTS

| | | | |
|---|---|---|---|
| 6,117,679 | A | 9/2000 | Stemmer |
| 6,376,246 | B1 | 4/2002 | Crameri et al. |
| 6,586,182 | B1 | 7/2003 | Patten et al. |
| 7,169,791 | B2 | 1/2007 | Breitenstein et al. |
| 7,569,566 | B2 | 8/2009 | Breitenstein et al. |
| 7,956,053 | B2 | 6/2011 | Breitenstein et al. |
| 2008/0220990 | A1 | 9/2008 | Fox |
| 2009/0312196 | A1 | 12/2009 | Colbeck et al. |
| 2010/0087463 | A1* | 4/2010 | Bruneau .............. A61K 9/1617 514/275 |

OTHER PUBLICATIONS

Manley, et al., Clinical and Preclinical Characterisation of the Metabolites of the BCR-ABL Tyrosine Kinase Inhibitor Nilotinib, Blood: 122 (21), p. 4011 (2013).*
Irby, R.B., et al., "Role of Src expression and activation in human cancer," Oncogene, 16:5636-5642 [2000].
Manley, P.W., et al., "Clinical and Preclinical Characterisation of the Metabolites of the BCR-ABL Tyrosine Kinase Inhibitor Nilotinib," Blood, 122(21):4011 [2013].
Paul, M.K., et al., "Tyrosine kinase—Role and significance in Cancer," Int. J. Med. Sci., 1(2):101-115 [2004].
Paul, S.M., et al., "How to improve R&D productivity: the pharmaceutical industry's grand challenge," Nat. Rev. Drug Disc., 9:203-214 [2010].

* cited by examiner

*Primary Examiner* — Erich A Leeser
(74) *Attorney, Agent, or Firm* — Codexis, Inc.

(57) ABSTRACT

The present invention provides kinase inhibitor analogs with improved properties, such as improved efficacy, pharmacokinetics, safety, and specificity. In some embodiments, the present invention provides nilotinib analogs that provide therapeutic benefits.

3 Claims, 2 Drawing Sheets

IMIDAZOYL ANILIDE DERIVATIVES AND METHODS OF USE

The present application is a national stage application filed under 35 USC § 371 and claims priority to PCT International Application No. PCT/US2015/047146, filed Aug. 27, 2015, which claims priority to previously filed U.S. Prov. Appln. Ser. Nos. 62/043,278, and 62/043,083, both of which were filed Aug. 28, 2014, all of which are hereby incorporated in their entireties for all purposes.

FIELD OF THE INVENTION

The present invention provides kinase inhibitor analogs with improved properties, such as improved efficacy, pharmacokinetics, safety, and specificity. In some embodiments, the present invention provides nilotinib analogs that provide therapeutic benefits.

BACKGROUND

Nilotinib (4-methyl-N-[3-(4-methyl-1H-imidazol-1-yl)-5-(trifluoromethyl)phenyl]-3-[(4-pyridin-3-ylpyrimidin-2-yl)amino]benzamide), is a small molecule tyrosine kinase inhibitor that has been approved for treatment of chronic myelogenous leukemia (CML). In particular, this compound has been used in treatment of CML that is resistant to another tyrosine kinase inhibitor, imatinib. It is also being investigated for use in treatment of Parkinson's disease, Alzheimer's disease, Huntington's disease, amyotrophic lateral sclerosis (ALS), and dementia.

However, while nilotinib appears to be relatively safe, there are various serious side-effects and contraindications associated with its use. For example, nilotinib administration has been associated with severe cardiovascular issues, including hypertension, arrhythmia, and prolonged QT interval. Indeed, sudden deaths have been reported, associated with nilotinib. Contraindications for use of nilotinib include long QT syndrome, hypokalaemia, hypomagnesaemia, pregnancy, planned pregnancy, lactation, and galactose/lactose intolerance. Caution is also indicated for use in patients with myelosuppression, tumor lysis syndrome, history of pancreatitis, and total gastrectomy. Thus, while nilotinib finds suitable use in some patients, there remains a need for compounds for the safe treatment of CML.

SUMMARY OF THE INVENTION

The present invention provides analogs of kinase inhibitors with improved properties, such as improved efficacy, pharmacokinetics, safety, and specificity when compared with the original kinase inhibitor. In some embodiments, the present invention provides nilotinib analogs with improved properties, such as improved efficacy, pharmacokinetics, safety, and specificity. In some embodiments, the present invention provides nilotinib analogs that provide therapeutic benefits.

In some embodiments, the present invention provides compounds comprising formula (I):

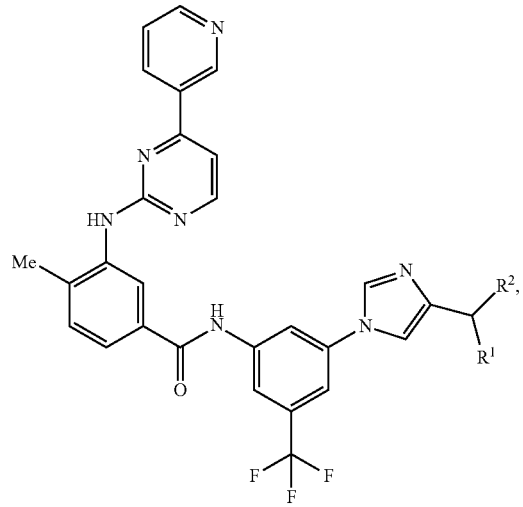

wherein $R^1$ and $R^2$ are independently selected from hydrogen, hydroxyl, alkyl, alkenyl, alkynyl, cycloalkyl, cycloalkylalkyl, aryl, arylalkyl, heteroaryl, heteroarylalkyl, heteroalkyl, heteroalkylaryl, alkoxy, aryloxy, carboxy, carboxyalkyl, carbonyloxy, substituted carbonyl, amino, substituted amino, aminoalkyl, halo, haloalkyl, hydroxyalkyl, thio, alkylthio, or sulfonyl each optionally substituted, or a salt thereof. In some additional embodiments, the compound is a salt. In some further embodiments, the compound is enantiomerically >97% pure. In some embodiments, the $R^1$=hydroxyl, alkoxy, aryloxy, amino, substituted amino, halo, haloalkyl, hydroxyalkyl, thio, alkylthio, or sulfonyl each optionally substituted and $R^2$=hydrogen, alkyl, cycloalkyl, cycloalkylalkyl, aryl, arylalkyl, heteroaryl, heteroarylalkyl, heteroalkyl, heteroalkylaryl, carboxy, carboxyalkyl, substituted carbonyl, carbonyloxy, aminoalkyl, haloalkyl, or hydroxyalkyl, wherein each is optionally substituted. In some further embodiments, the $R^1$=hydroxy, alkoxy, carbonyloxy, substituted amino, or halo and $R^2$=hydrogen or alkyl. In still some additional embodiments, the compound comprises one of the following structures:

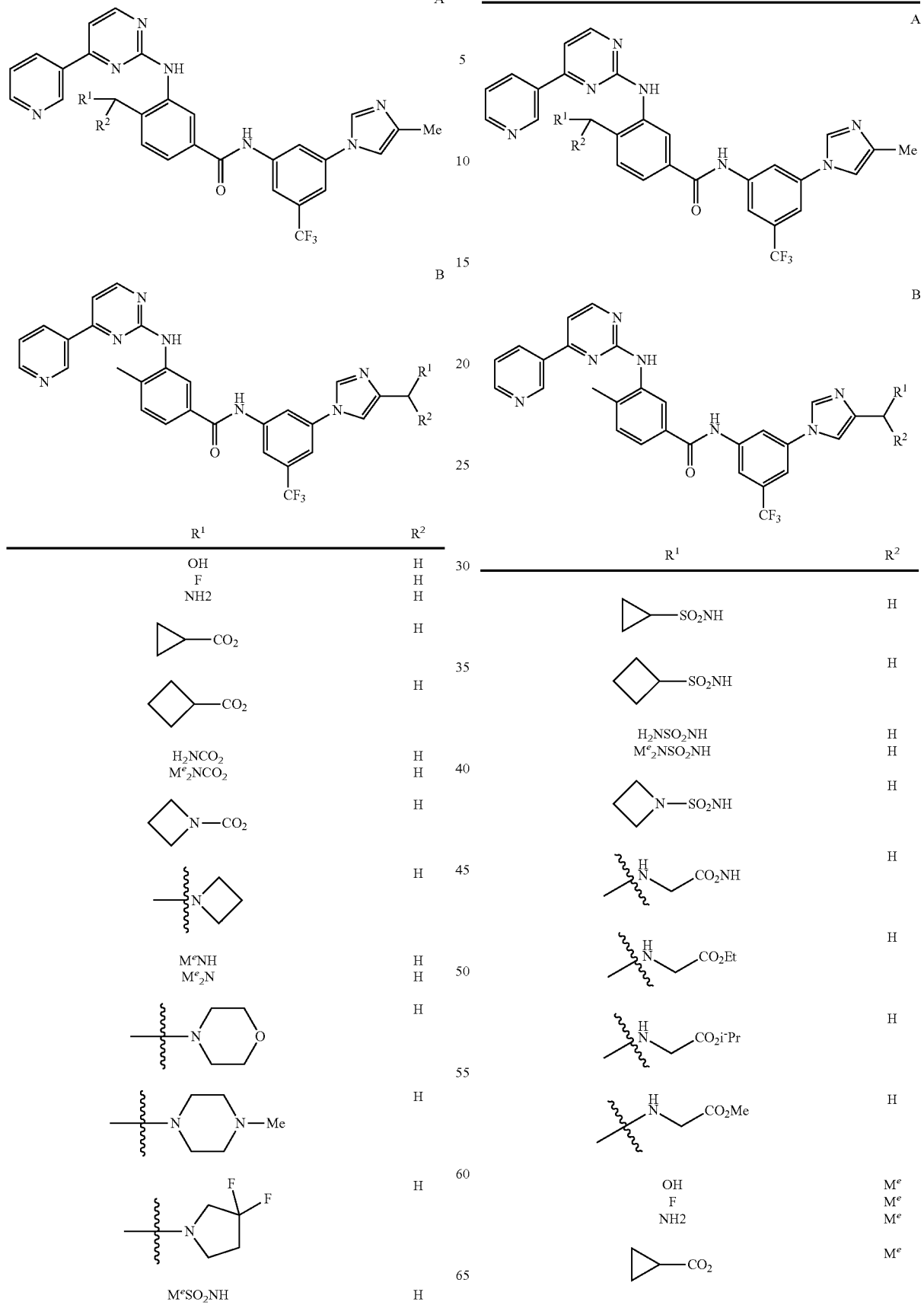

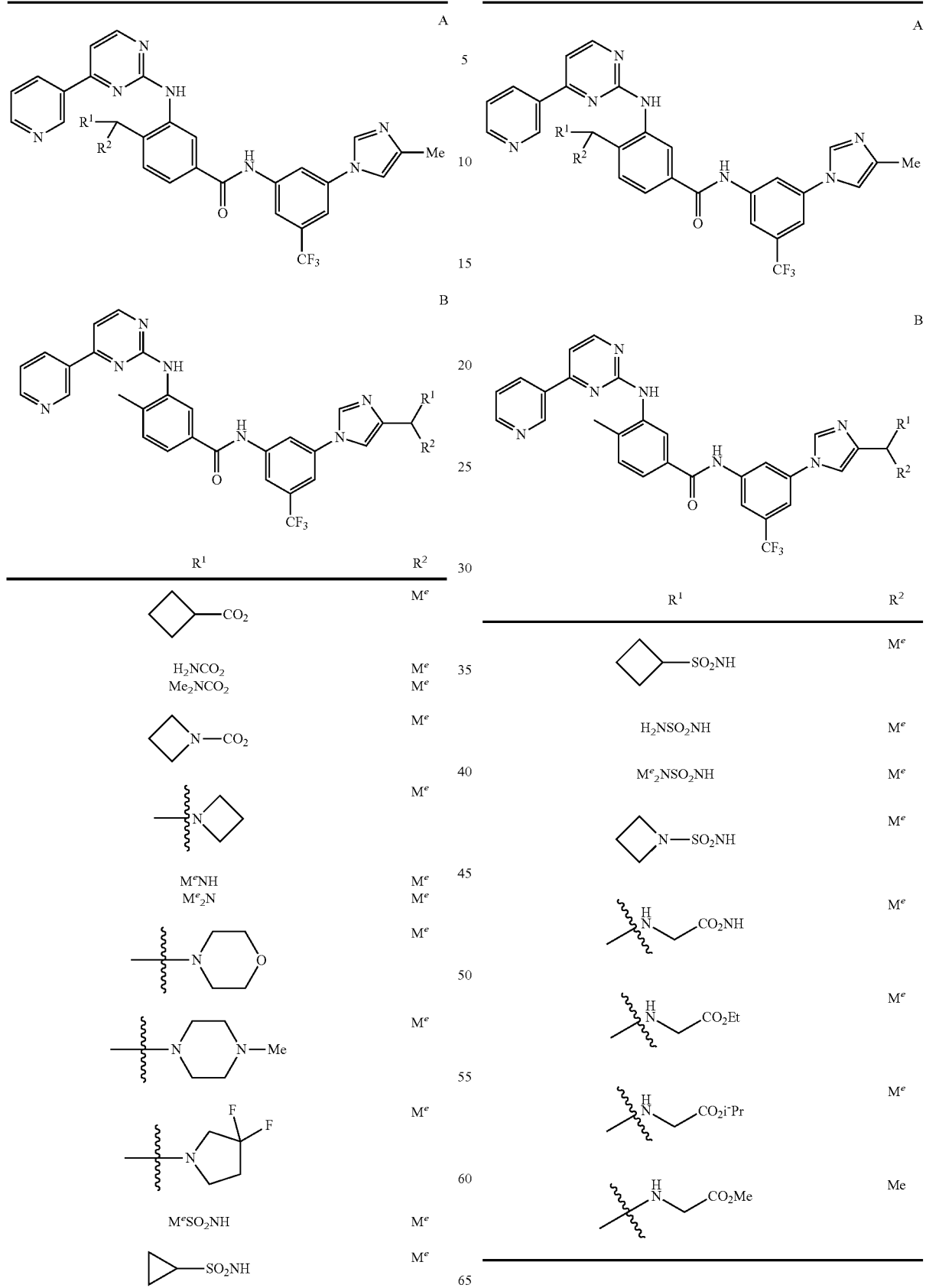
In some additional further embodiments, the compound comprises one of the following structures:

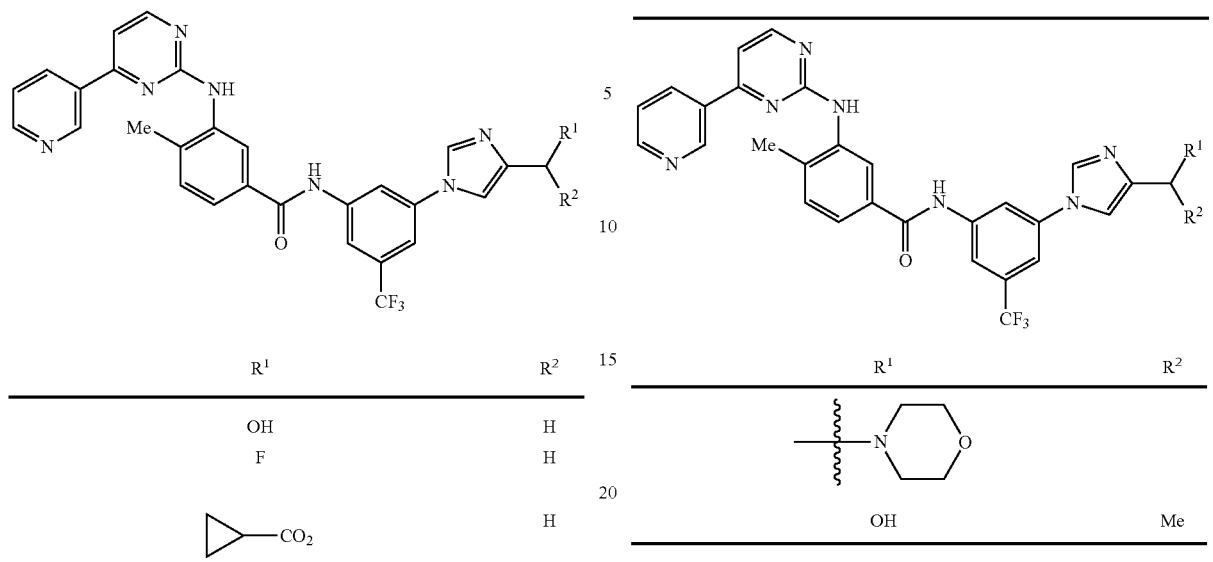

| R¹ | R² |
|---|---|
| OH | H |
| F | H |
| cyclopropyl-CO₂ | H |
| 3,3-difluoropyrrolidin-1-yl | H |
| H₂NCO₂ | H |
| NH-CH₂-CO₂H | H |
| NH-CH₂-CO₂Me | H |
| 4-methylpiperazin-1-yl | H |
| azetidin-1-yl | H |
| MeNH | H |
| Me₂N | H |
| morpholin-4-yl | — |
| OH | Me |

The present invention also provides compositions comprising the compound of formula (II):

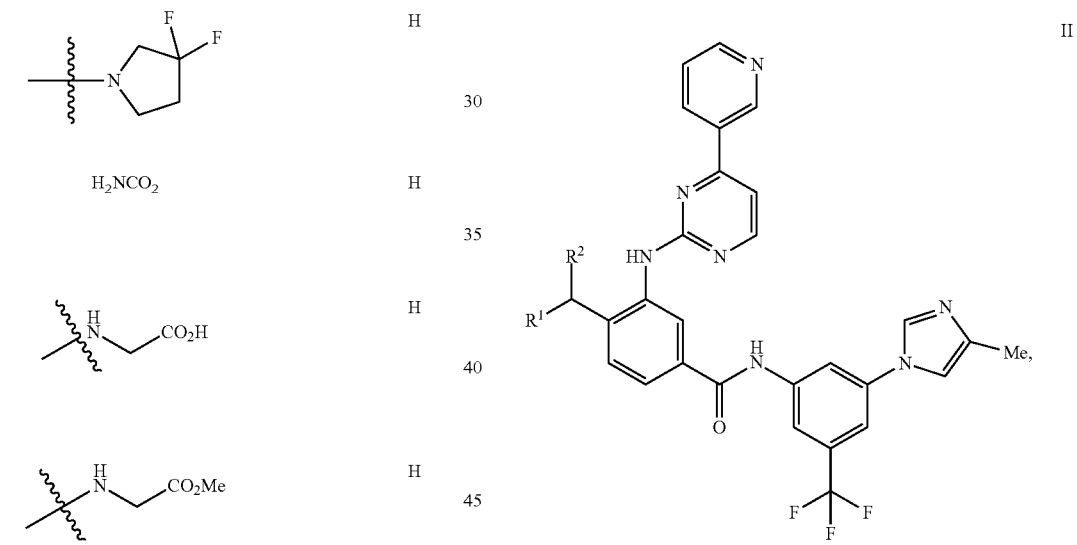

wherein $R^1$ and $R^2$ are independently selected from hydrogen, hydroxyl, alkyl, alkenyl, alkynyl, cycloalkyl, cycloalkylalkyl, aryl, arylalkyl, heteroaryl, heteroarylalkyl, heteroalkyl, heteroalkylaryl, alkoxy, aryloxy, carboxy, carboxyalkyl, substituted carbonyl, carbonyloxy, amino, substituted amino, aminoalkyl, halo, haloalkyl, hydroxyalkyl, thio, alkylthio, or sulfonyl each optionally substituted. In some additional embodiments, the compound is a salt. In some further embodiments, the compound is enantiomerically >97% pure. In some embodiments, the $R^1$=hydroxyl, alkoxy, aryloxy, amino, substituted amino, halo, haloalkyl, hydroxyalkyl, thio, alkylthio, or sulfonyl each optionally substituted and R=hydrogen, alkyl, cycloalkyl, cycloalkylalkyl, aryl, arylalkyl, heteroaryl, heteroarylalkyl, heteroalkyl, heteroalkylaryl, carboxy, carboxyalkyl, substituted carbonyl, carbonyloxy, aminoalkyl, haloalkyl, or hydroxyalkyl, each optionally substituted. In some additional embodiments $R^1$=hydroxy, alkoxy, carbonyloxy, substituted amino, or halo and $R^2$=hydrogen or alkyl. In some further embodiments, the compound comprises one of the following structures:

| 9 | 10 |
|---|---|
| A | A (-continued) |

Structure A (same on both columns 9 and 10): 3-pyridyl-pyrimidin-2-ylamino substituted benzamide with N-(3-(4-methylimidazol-1-yl)-5-trifluoromethylphenyl), bearing R¹/R² substituents on a CH group attached to the central phenyl ring.

Structure B (same on both columns 9 and 10): 3-pyridyl-pyrimidin-2-ylamino substituted 4-methylbenzamide with N-(3-(imidazol-1-yl)-5-trifluoromethylphenyl), bearing R¹/R² substituents on a CH of the imidazole side.

Column 9:

| R¹ | R² |
|---|---|
| OH | H |
| F | H |
| NH2 | H |
| cyclopropyl-CO₂ | H |
| cyclobutyl-CO₂ | H |
| H₂NCO₂ | H |
| Me₂NCO₂ | H |
| azetidin-N-CO₂ | H |
| azetidin-1-yl (N-linked via CH) | H |
| MeNH | H |
| Me₂N | H |
| morpholin-4-yl | H |
| 4-methylpiperazin-1-yl | H |
| 3,3-difluoropyrrolidin-1-yl | H |

Column 10:

| R¹ | R² |
|---|---|
| MeSO₂NH | H |
| cyclopropyl-SO₂NH | H |
| cyclobutyl-SO₂NH | H |
| H₂NSO₂NH | H |
| Me₂NSO₂NH | H |
| azetidin-N—SO₂NH | H |
| —NH—CH₂—CO₂H | H |
| —NH—CH₂—CO₂Et | H |
| —NH—CH₂—CO₂iPr | H |
| —NH—CH₂—CO₂Me | H |
| OH | Me |
| F | Me |
| NH2 | Me |
| cyclopropyl-CO₂ | Me |

In some additional embodiments, the compound comprises one of the following structures:

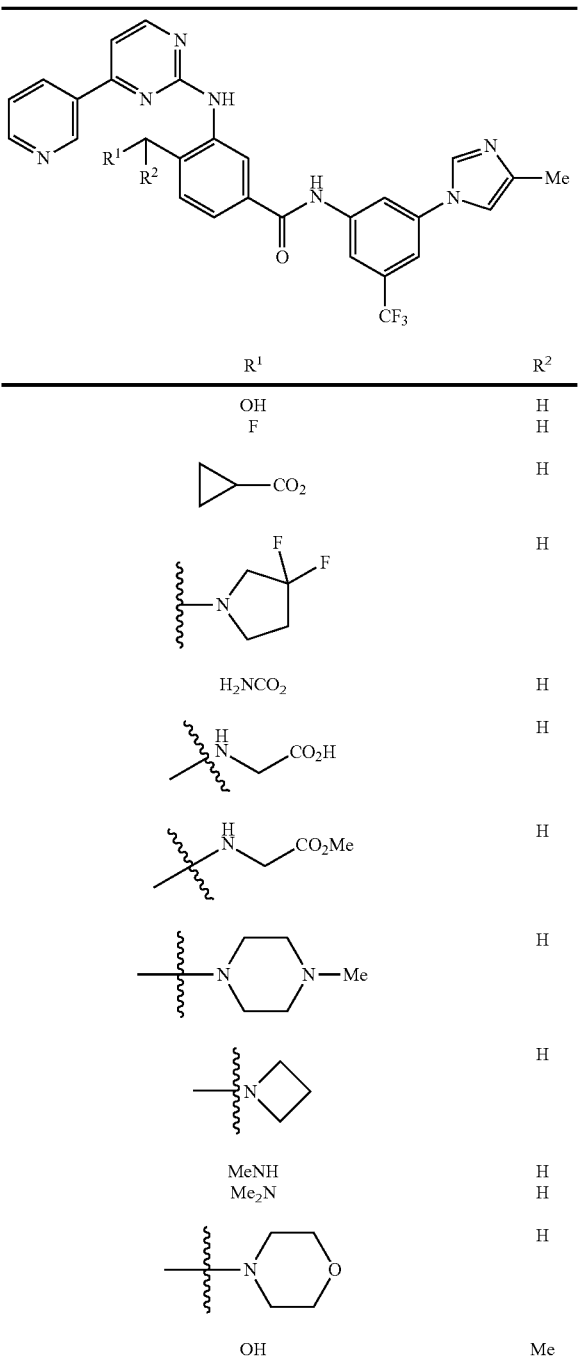

| R¹ | R² |
|---|---|
| OH | H |
| F | H |
| cyclopropyl-CO₂ | H |
| 3,3-difluoropyrrolidinyl | H |
| H₂NCO₂ | H |
| NH-CH₂-CO₂H | H |
| NH-CH₂-CO₂Me | H |
| 4-methylpiperazinyl | H |
| azetidinyl | H |
| MeNH | H |
| Me₂N | H |
| morpholinyl | H |
| OH | Me |

The present invention further provides compounds 2 through 22, as provided herein, as well as any suitable derivatives (e.g., salts, alcohols, etc.), thereof.

The present invention also provides compositions comprising the compounds provided herein (i.e., compounds 2 through 21) in various compositions (e.g., pharmaceutical compositions/formulations). In some embodiments, these compositions find use in treating disease. In some additional embodiments, these compounds and/or compositions are administered to an animal. In some embodiments, the compositions and/or compounds are administered to humans. However, it is not intended that the present invention be limited to the use of the present compounds and/or compositions comprising them in the field of human medical treatment, as it is contemplated that the compounds and/or compositions comprising them will find use in other suitable fields.

The present invention also provides methods for generating improved kinase inhibitor analogs. In some embodiments, the methods comprise exposing a starting kinase inhibitor to a cytochrome P450 monooxygenase to produce an analog, purifying said analog, and determining the kinase inhibition activity of said analog. In embodiments, the kinase inhibitor analog comprises an introduced hydroxyl moiety. In some further embodiments, the kinase inhibitor is further modified to provide additional kinase inhibitors. In some additional embodiments, the site of hydroxylation is further modified chemically to provide new kinase inhibitors. In still some further embodiments, the starting kinase inhibitor is nilotinib. In some additional embodiments, the starting kinase inhibitor is a known kinase inhibitor.

DESCRIPTION OF THE INVENTION

Figure 1:
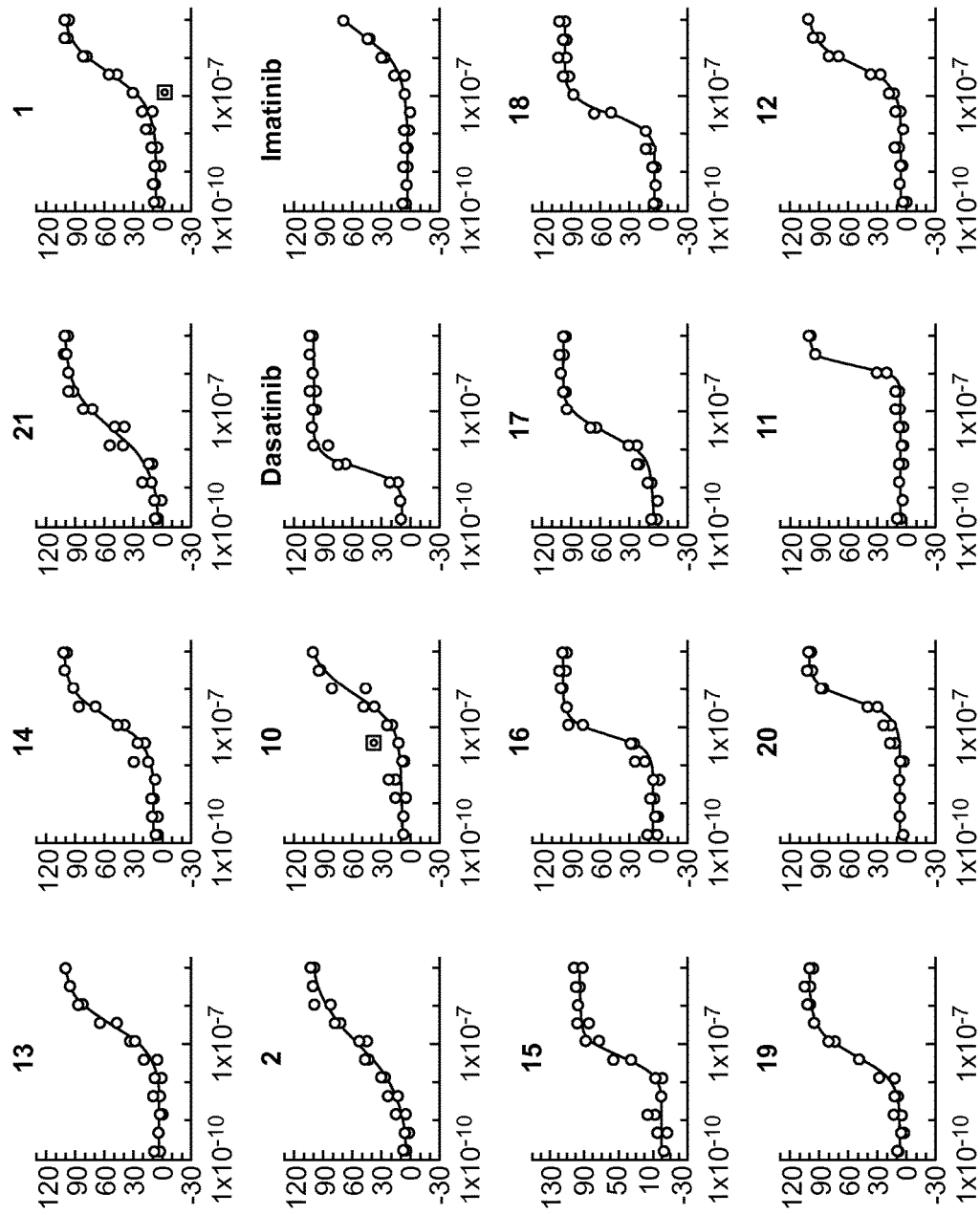
FIG. 1 provides graphs showing the Abl inhibition results obtained with various analogs FIG. 2 provides graphs showing the cytotoxicity results obtained with various analogs.

The present invention provides kinase inhibitor analogs with improved properties, such as improved efficacy, pharmacokinetics, safety, and specificity. In some embodiments, the present invention provides nilotinib analogs that provide therapeutic benefits.

All patents and publications, including all sequences disclosed within such patents and publications, referred to herein are expressly incorporated by reference. Unless otherwise indicated, the practice of the present invention involves conventional techniques commonly used in pharmacology, molecular biology, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, some methods and materials are described herein. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Definitions

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, small molecule, etc.) or other component that is removed from at least one other component with which it is naturally associated or is typically associated with during synthesis.

As used herein, the term "wild-type" refers to naturally-occurring organisms, enzymes and/or other proteins (e.g., non-recombinant proteins).

As used herein, "nilotinib" refers to the molecule 4-methyl-N-[3-(4-methyl-1H-imidazol-1-yl)-5-(trifluoromethyl)phenyl]-3-[(4-pyridin-3-ylpyrimidin-2-yl)amino]benzamide, As used herein, "analog" refers to a compound that resembles another compound with respect to structure and/or function. The present invention provides nilotinib analogs with improved properties, as compared to nilotinib.

The terms "improved" or "improved properties," as used in the context of describing the properties of a nilotinib analog (e.g., nilotinib analog variants), refers to a nilotinib analog that exhibits an improvement in a property or properties as compared to another nilotinib analog and/or a specified reference tyrosine kinase or nilotinib analog. Improved properties include, but are not limited to such properties as improved pharmacokinetics (e.g., lower clearance, longer half life, favorable distribution, improved bioavailability, etc.), reduced safety liabilities (e.g., reduced interaction with undesirable targets, such as hERG, liver CYPS, etc.), differential kinase specificity, and any other relevant properties taken into consideration during drug development.

As used herein, the term "tyrosine kinase" refers to protein kinase enzymes that are involved in various cell functions, including cell signaling, growth, and division through phosphorylation of proteins by the transfer of phosphate groups from ATP to proteins. Tyrosine phosphorylation by tyrosine kinases modulates enzymatic activity and creates binding sites used in recruitment of downstream signaling proteins. Tyrosine kinases are classified as receptor tyrosine kinases (RTK; e.g., EGFR, PDGFR, and FGFR, etc.) and non-receptor tyrosine kinases (NRTK; e.g., SRC, ABL, FAK, etc.) (See e.g., Paul and Mukhopadhyay, Int. J. Med. Sci., 1:101-115 [2004]). In addition to being kinases, the RTKs are cell surface transmembrane receptors. NRTKs are cytoplasmic proteins with a kinase domain and other signaling or protein-protein interacting domains. Tyrosine kinases either directly or indirectly participate in the signal transduction pathways of a variety of cellular activities, including proliferation, adhesion, migration and differentiation. As tyrosine kinases are critical components in cell signaling pathways, their activity is highly regulated in normal cells. However, if the enzyme is mutated or otherwise impacted, malignancy can occur (e.g., "oncogenic tyrosine kinase"). Diseases associated with tyrosine kinase activity include proliferation of tumor cells, pathological neovascularization that promotes the growth of solid tumors, ocular neovascularization (diabetic retinopathy, age-induced macular degeneration and the like) and inflammation (psoriasis, rheumatoid arthritis and the like).

As used herein, the term "kinase inhibitor" and "inhibitor of kinase activity" refer to compounds that interact with at least one kinase and inhibit the enzymatic activity of the kinase(s).

As used herein, the term "inhibiting kinase activity" refers to reducing the ability of a kinase to transfer a phosphate group from a donor molecule (e.g., ATP) to a specific target molecule (i.e., a substrate). In some embodiments, the inhibition of kinase activity is at least about 10%, as compared to an uninhibited kinase. In some other embodiments, the reduction in kinase activity is at least about 25%, at least about 50%, at least about 75%, at least about 90%, at least about 95%, at least about 99%, or 100%, as compared to uninhibited kinase.

As used herein, the "$IC_{50}$ value" refers to the concentration of kinase inhibitor that reduces the activity of a kinase to 50% of that of an uninhibited enzyme.

As used herein, the term "inhibiting effective amount" refers to a dosage sufficient to cause kinase activity inhibition.

In some embodiments, the inhibition is "specific," that the kinase inhibitor reduces the ability of a kinase to transfer a phosphate group from a donor molecule (e.g., ATP) to a specific target molecule (e.g., a substrate, such as tyrosine) at a concentration that is lower than the concentration of the inhibitor that is required to produce another, unrelated biological effect. In some embodiments, the concentration of inhibitor required for kinase inhibitory activity is at least 2-fold lower, at least 5-fold lower, at least 10-fold lower, at least 20-fold lower, or at least 25-fold lower than the concentration of the inhibitor to produce an unrelated biological effect.

As used herein, the terms "tyrosine kinase inhibitor," "tyrphostin," "tyrosine phosphorylation inhibitor," and "TKI" refer to drugs that inhibit tyrosine kinases. These TKIs are often effective in treating malignancies. In general, they compete with the ATP binding site of the catalytic domain of oncogenic tyrosine kinases. These inhibitors interfere with specific cell signaling pathways and provide target-specific therapy for certain malignancies.

As used herein, the term "tyrosine kinase-induced diseases or conditions" refers to pathological conditions that depend upon the activity of at least one tyrosine kinase.

As used herein, "CML" refers to chronic myelogenous leukemia. In some embodiments, the term refers to Philadelphia chromosome-positive (Ph+) CML.

As used herein, "Abl" ("ABL") and "Abl1" ("ABL1") refer to the Abelson murine leukemia viral oncogene homolog 1, which is a protein encoded by the ABL1 gene in humans. The Abl1 proto-oncogene encodes cytoplasmic and nuclear tyrosine kinases implicated in cell differentiation, cell division, cell adhesion, and the stress response. Mutations in the Abl1 gene are associated with CML. In CML cases, the Abl gene is activated by being translocated within the breakpoint cluster region (BCR) gene. The resulting fusion gene (BCR-ABL) encodes an unregulated, cytoplasmic-targeted tyrosine kinase that permits cell proliferation that is unregulated by cytokines, leading to cancer.

As used herein, "ckit," also referred to as "CD117" and "stem cell factor receptor" refers to a cell surface protein receptor present on various cells. It binds stem cell factor (SCF), which results in the growth of certain hematopoietic cells and other cell types.

As used herein, "cSRC," also referred to as "proto-oncogene tyrosine protein kinase Src," and "proto-oncogene c-Src" refer to a non-receptor protein tyrosine kinase encoded by the SRC gene in humans. It is associated with cancer progression due to its interaction with other cell signals.

As used herein, Flt1," also referred to as "tyrosine-protein kinase receptor FLT," and Fms-related tyrosine kinase 1," refer to a receptor tyrosine kinase (RTK) that is important in angiogenesis and vasculogenesis.

As used herein, "PDGFR," also referred to as "platelet-derived growth factor receptor" refer to cell surface tyrosine kinase receptors for platelet-derived growth factors (PDGF). There are alpha (α) and beta (β) subunits of these receptors, each of which are encoded by different genes. The PDGF family plays important roles in regulating cell proliferation, cellular differentiation, and cell growth.

As used herein, the term "medicament" refers any substance suitable for medical and/or veterinary use in treating any disease or condition.

As used herein, the term "pharmaceutical formulation" refers to compositions (i.e., medicaments) in any formulation suitable for administration to humans and/or other animals. As used herein, the pharmaceutical formulations of the present invention comprise at least one nilotinib analog provided herein. It is not intended that the present invention be limited to any particular type of formulation, as liquid, solid, emulsions and any other suitable formulations find use in the present invention. It is intended that any suitable means of administration of the pharmaceutical formulations find use in the present invention, including but not limited to intravenous, subcutaneous, oral, rectal, etc. It is also intended that the formulations are in any suitable format (e.g., tablets, capsules, suppositories, liquids, gels, emulsions, etc.).

As used herein, the term "pharmaceutically acceptable salt" in the present invention refers to an active ingredient which comprises at least one nilotinib analog provided herein in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of the active ingredient, with respect to its therapeutic efficacy in vivo.

The present invention furthermore provides medicaments comprising at least one nilotinib analog of the present invention and/or pharmaceutically useful salts and stereoisomers thereof, including mixtures in all ratios, and optionally excipients and/or adjuvants.

As used herein, the terms "administration" and "administering" refer to the introduction of a composition (e.g., a pharmaceutical formulation) into or on the body of a human or other animal.

As used herein, the term "therapeutically effective" refers to the ability of a pharmaceutical formulation to effectively treat the disease and/or condition for which it is administered to a human or other animal.

As used herein the term "therapeutically effective amount" refers to the amount and/or concentration of a composition (e.g., pharmaceutical formulation), that when administered to a patient, elicits the desired therapeutic effect. In some embodiments, the therapeutic effect is dependent upon the disease being treated and the desired results, as well as the individual patient (e.g., weight, stage of disease, physical and/or psychological condition, etc.).

As used herein, the terms "treating cancer" and "treatment of cancer" refer to administration of at least one composition to a mammal afflicted with a cancerous condition under conditions such that the cancerous condition is reduced or eliminated.

As used herein, "conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a polypeptide can be expressed as "percent conversion" of the substrate to the product.

As used herein, "suitable reaction conditions" refer to those conditions in the biocatalytic reaction solution (e.g., ranges of enzyme loading, substrate loading, cofactor loading, temperature, pH, buffers, co-solvents, etc.) under which a compound of the present invention is capable of converting a substrate compound to a product compound. Exemplary "suitable reaction conditions" are provided in the present disclosure and illustrated by the Examples.

As used herein, "loading", such as in "compound loading" or "enzyme loading" or "cofactor loading" refers to the concentration or amount of a component in a reaction mixture at the start of the reaction.

As used herein, "substrate," used in the context of a biocatalyst mediated process refers to the compound or molecule acted on by the biocatalyst.

As used herein, "product" used in the context of a biocatalyst mediated process refers to the compound or molecule resulting from the action of the biocatalyst.

As used herein, the term "Cyp" refers to cytochrome P450 monooxygenase. In some embodiments, the present invention comprises the use of cytochrome P450 monooxygenase variants (i.e., recombinant cytochrome P450 monooxygenase enzymes).

As used herein, "alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., $(C_1-C_6)$ alkyl refers to an alkyl of 1 to 6 carbon atoms.

As used herein, "alkenyl" refers to groups of from 2 to 12 carbon atoms inclusively, either straight or branched containing at least one double bond but optionally containing more than one double bond.

As used herein, "alkynyl" refers to groups of from 2 to 12 carbon atoms inclusively, either straight or branched containing at least one triple bond but optionally containing more than one triple bond, and additionally optionally containing one or more double bonded moieties.

As used herein, "cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

As used herein, "cycloalkylalkyl" refers to an alkyl substituted with a cycloalkyl, i.e., cycloalkyl-alkyl-groups, preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

As used herein, "aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

As used herein, "arylalkyl" refers to an alkyl substituted with an aryl (i.e., aryl-alkyl-groups), preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

As used herein, "heteroalkyl, "heteroalkenyl." and heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—. —NR$^\gamma$—, —PH—, —S(O)—, —S(O)$_2$—, —S(O)NR$^\gamma$—, —S(O)$_2$NR$^\gamma$—, and the like, including combinations thereof, where each R$^\gamma$ is independently selected from hydrogen, alkyl, heteroalkyl, cycloalkyl, heterocycloalkyl, aryl, and heteroaryl.

As used herein, "heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

As used herein, "heteroarylalkyl" refers to an alkyl substituted with a heteroaryl, i.e., heteroaryl-alkyl-groups, preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

As used herein, "heterocycle," "heterocyclic," and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

As used herein, "heterocycloalkylalkyl" refers to an alkyl substituted with a heterocycloalkyl (i.e., heterocycloalkyl-alkyl-groups), preferably having from 1 to 6 carbon atoms inclusively in the alkyl moiety and from 3 to 12 ring atoms inclusively in the heterocycloalkyl moiety.

As used herein, "oxy" refers to a divalent group —O—, which may have various substituents to form different oxy groups, including ethers and esters.

As used herein, "alkoxy" or "alkyloxy" are used interchangeably herein to refer to the group —OR$^\xi$, wherein R$^\xi$ is an alkyl group, including optionally substituted alkyl groups.

As used herein, "aryloxy" as used herein refer to the group —OR wherein R is an aryl group as defined above including optionally substituted aryl groups as also defined herein.

As used herein, "carbonyloxy" refers to the group —O(CO)R wherein R is selected from hydrogen or optionally substituted alkyl, cycloalkyl, cycloheteroalkyl, alkoxy, carboxy, aryl, aryloxy, amino, substituted amino, heteroaryl, heteroalkyl, heteroalkylalkyl, heteroarylalkyl, and the like.

As used herein, "carboxy" refers to —COOH.

As used herein, "carboxyalkyl" refers to an alkyl substituted with a carboxy group.

As used herein, "carbonyl" refers to the group —C(O)—. Substituted carbonyl refers to the group R$^\eta$—C(O)—R$^\eta$, where each R$^\eta$ is independently selected from optionally substituted alkyl, cycloalkyl, cycloheteroalkyl, alkoxy, carboxy, aryl, aryloxy, heteroaryl, heteroarylalkyl, acyl, alkoxycarbonyl, sulfanyl, sulfinyl, sulfonyl, and the like. Typical substituted carbonyl groups including acids, ketones, aldehydes, amides, esters, acyl halides, thioesters, and the like.

As used herein, "amino" refers to the group —NH$_2$. Substituted amino refers to the group —NHR$^\eta$, NR$^\eta$R$^\eta$, and NR$^\eta$R$^\eta$R$^\eta$, where each R$^\eta$ is independently selected from optionally substituted alkyl, cycloalkyl, cycloheteroalkyl, alkoxy, carboxy, aryl, aryloxy, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylsulfonylamino, furanyl-oxy-sulfamino, and the like. A substituted amino group —N R$^\eta$R$^\eta$, can also comprise a heterocycle with attachment at nitrogen, examples include azetidine, morpholine, etc. This hetocycle can also form part of a spirocyclic, bridged- or fused-bicyclic system.

As used herein, "aminoalkyl" refers to an alkyl group in which one or more of the hydrogen atoms are replaced with an amino group, including a substituted amino group.

As used herein, "aminocarbonyl" refers to a carbonyl group substituted with an amino group, including a substituted amino group, as defined herein, and includes amides.

As used herein, "aminocarbonylalkyl" refers to an alkyl substituted with an aminocarbonyl group, as defined herein.

As used herein, "halogen" and "halo" refer to fluoro, chloro, bromo and iodo.

As used herein, "haloalkyl" refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C$_1$ C$_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

As used herein, "hydroxy" refers to —OH.

As used herein, "hydroxyalkyl" refers to an alkyl substituted with one or more hydroxy group.

As used herein, "thio" and "sulfanyl" refer to —SH. Substituted thio or sulfanyl refers to —S—R$^\eta$, where R$^\eta$ is an alkyl, aryl or other suitable substituent.

As used herein, "alkylthio" refers to —SR$^\xi$ where R$^\xi$ is an alkyl, which can be optionally substituted. Typical alkylthio group include, but are not limited to, methylthio, ethylthio, n-propylthio, and the like.

As used herein, "alkylthioalkyl" refers to an alkyl substituted with an alkylthio group, —SR$^\zeta$, where R$^\zeta$ is an alkyl, which can be optionally substituted.

As used herein, "sulfonyl" refers to —SO$_2$—. Substituted sulfonyl refers to —SO$_2$—R$^\eta$, where R$^\eta$ is an alkyl, aryl or other suitable substituent.

As used herein, "alkylsulfonyl" refers to —SO$_2$—R$^\zeta$, where R$^\zeta$ is an alkyl, which can be optionally substituted. Typical alkylsulfonyl groups include, but are not limited to, methylsulfonyl, ethylsulfonyl, n-propylsulfonyl, and the like.

As used herein, "alkylsulfonylalkyl" refers to an alkyl substituted with an alkylsulfonyl group, —SO$_2$—R$^\zeta$, where R$^\zeta$ is an alkyl, which can be optionally substituted.

As used herein, "membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

As used herein, "fused bicyclic ring" refers to both unsubstituted and substituted carbocyclic and/or heterocyclic ring moieties having 5 or 8 atoms in each ring, the rings having 2 common atoms.

As used herein, "optionally substituted" as used herein with respect to the foregoing chemical groups means that positions of the chemical group occupied by hydrogen can be substituted with another atom, such as carbon, oxygen, nitrogen, or sulfur, or a chemical group, exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; where preferred heteroatoms are oxygen, nitrogen, and sulfur. Additionally, where open valences exist on these substitute chemical groups they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further contemplated that the above substitutions can be made provided that replacing the hydrogen with the substituent does not introduce unacceptable instability to the molecules of the present disclosure, and is otherwise chemically reasonable. One of ordinary skill in the art would understand that with respect to any chemical group described as optionally substituted, only sterically practical and/or synthetically feasible chemical groups are meant to be included. Finally, "optionally substituted" as used herein refers to all subsequent modifiers in a term or series of chemical groups. For example, in the term "optionally substituted arylalkyl," the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention.

As used herein, "recombinant" used in reference to a cell or vector, refers to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. Thus. "recombinant" or "engineered" or "non-naturally occurring" when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level. "Recombination," "recombining" and generating a "recombined" nucleic acid generally encompass the assembly of at least two nucleic acid fragments. In some embodiments, "Recombination." "recombining," and generating a "recombined" nucleic acid also encompass the assembly of two or more nucleic acid fragments wherein the assembly gives rise to a chimeric gene.

General Description of the Compounds of the Present Invention.

In some embodiments, the compounds of the present invention comprise analogs of pharmaceutically active molecules that are generated via hydroxylation of a pharmaceutically active molecule, followed by further chemical or biocatalytic modification of such hydroxylated pharmaceutically active molecules. In some embodiments, the pharmaceutically active molecules are tyrosine kinase inhibitors, and the compounds of the present invention are substituted derivatives of the hydroxylated analogs of the tyrosine kinase inhibitors.

In some embodiments, the present invention provides a compound of formula I, wherein a hydrogen atom is replaced by a hydroxyl group (—OH) to give a compound that is chemically stable (i.e., does not spontaneously degrade).

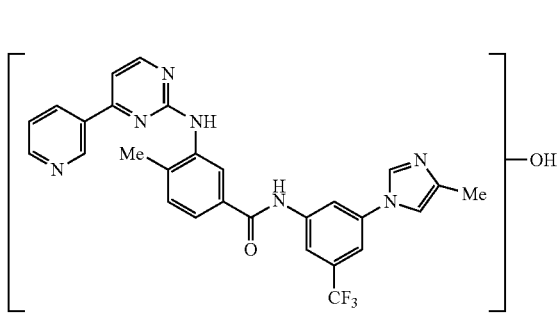

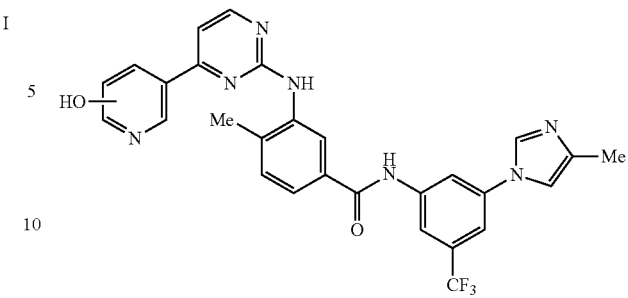

In some additional embodiments, the present invention provides a compound of formula II wherein a nitrogen atom on a heteroaryl group is oxidized to give the N-oxide that is chemically stable (i.e., does not spontaneously degrade).

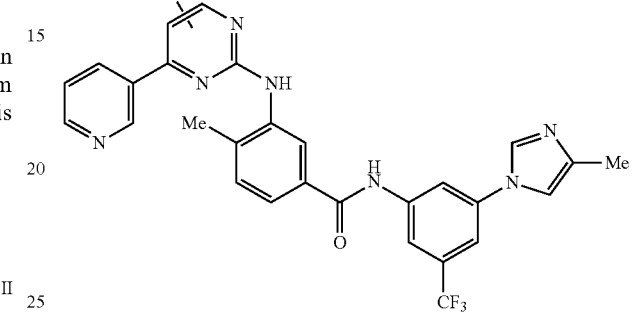

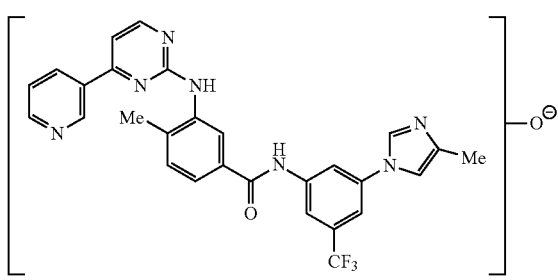

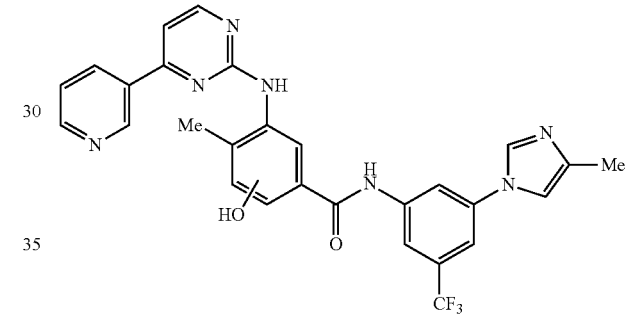

In some further embodiments, the present invention provides a compound of formula III which is prepared from a compound of type I or II or derived from a compound of formula I or II, wherein R is optionally substituted alkyl, alkenyl, alkynyl, cycloalkyl, cycloalkylalkyl, aryl, arylalkyl, heteroaryl, heteroarylalkyl, heteroalkyl, heteroalkylaryl, alkoxy, aryloxy, carboxy, carboxyalkyl, substituted carbonyl, carbonyloxy, amino, substituted amino, aminoalkyl, halo, haloalkyl, hydroxyalkyl, thio, alkylthio, or sulfonyl.

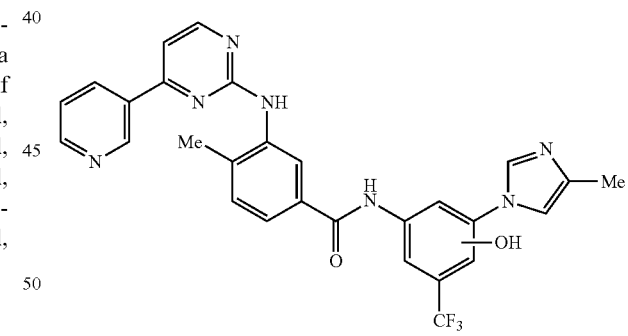

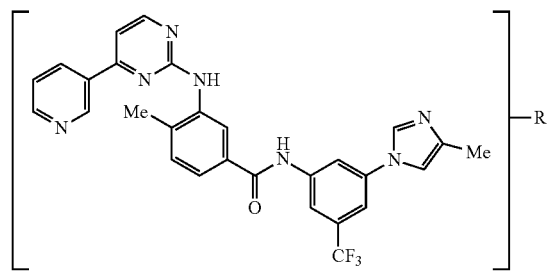

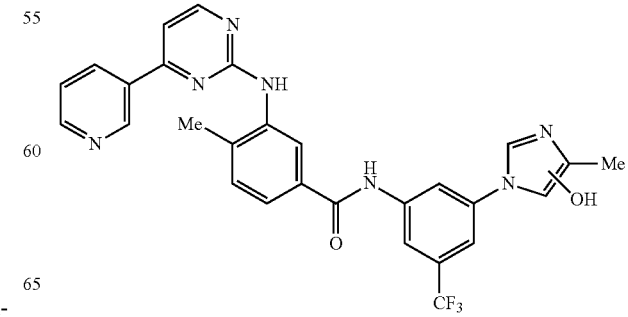

In still some additional embodiments, the present invention provides compounds with the following formulae:

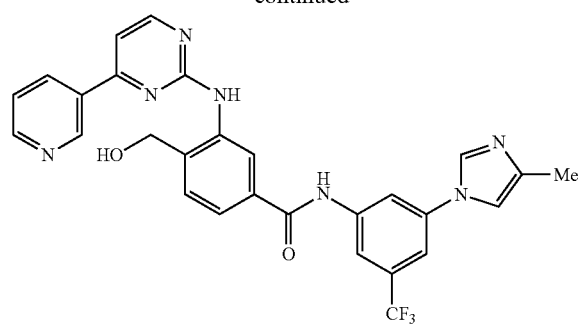
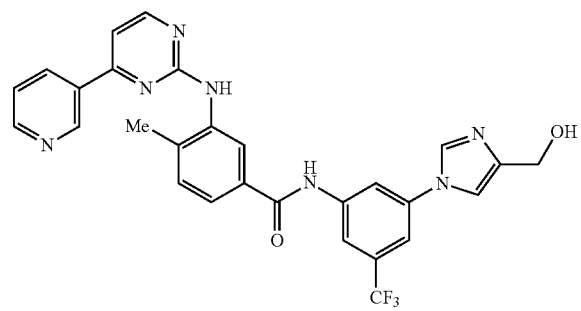
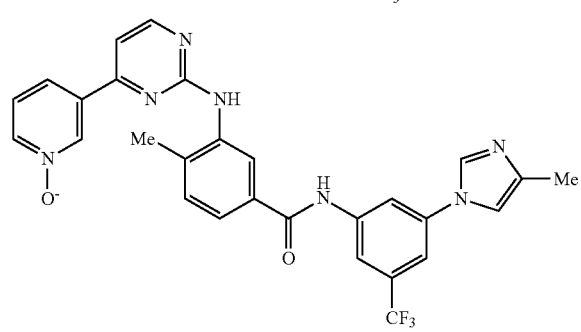
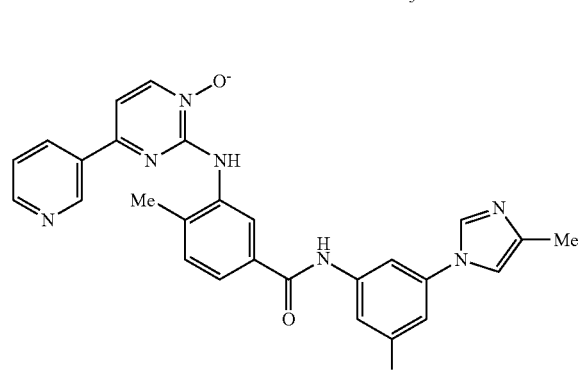
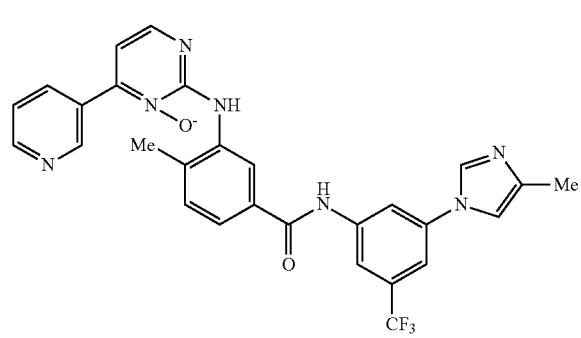
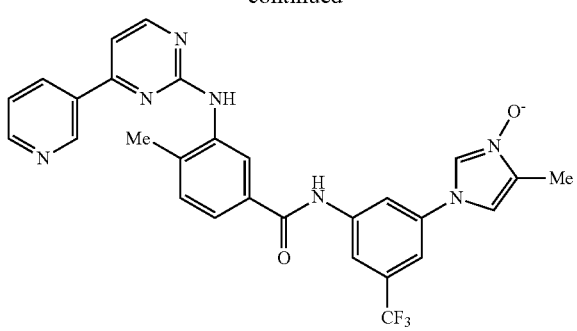
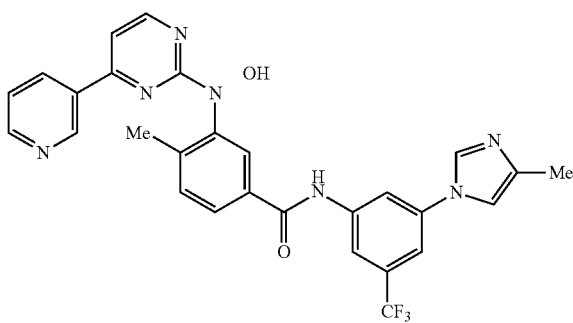
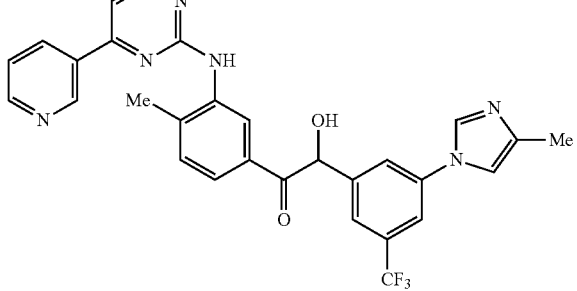
In some embodiments, the present invention provides compounds with the following formulae, wherein R is optionally substituted alkyl, aryl, cycloalkyl, heteroalkyl, heteroaryl, alkoxy, aryloxy, carboxy, amino, substituted amino, halo, carbonyloxy, hydroxylalkyl, alkylthio, substituted carbonyl or sulfonyl.
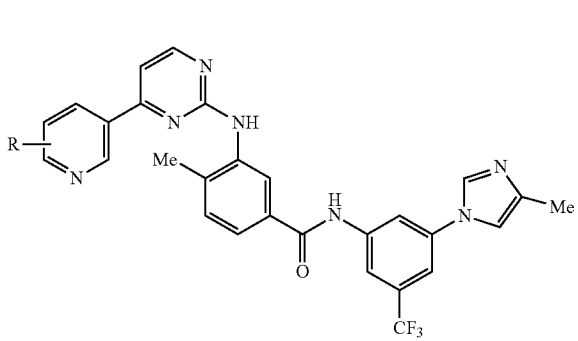

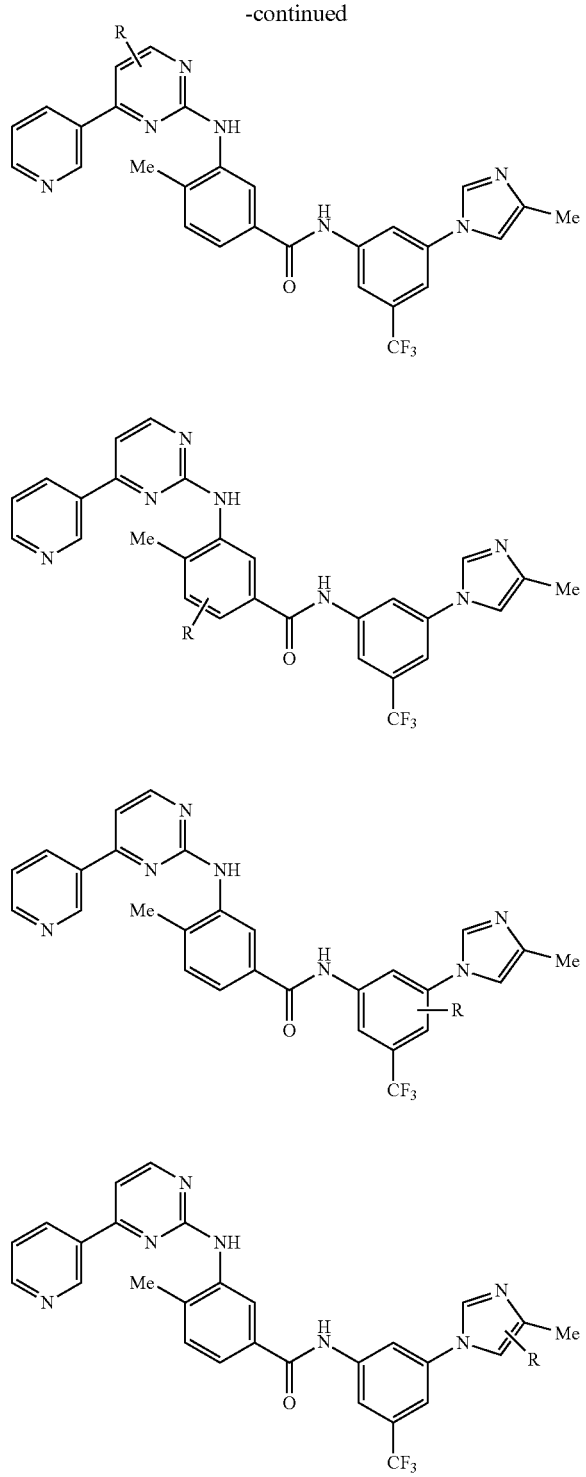

In some additional embodiments, the present invention provides compounds with the following formulae, wherein $R^1$, $R^2$ are independently optionally hydrogen, hydroxyl, or substituted alkyl, alkenyl, alkynyl, cycloalkyl, cycloalkylalkyl, aryl, arylalkyl, heteroaryl, heteroarylalkyl, heteroalkyl, heteroalkylaryl, alkoxy, aryloxy, carboxy, carbonyloxy, carboxyalkyl, substituted carbonyl, amino, substituted amino, aminoalkyl, halo, haloalkyl, hydroxyalkyl, thio, alkylthio, or sulfonyl.

In some further embodiments, the present invention provides compounds with the following formulae, wherein R alkyl, cycloalkyl, cycloalkylalkyl, aryl, arylalkyl, heteroaryl, heteroarylalkyl, heteroalkyl, heteroalkylaryl, alkoxy, aryloxy, carboxyalkyl, carbonyloxy, substituted carbonyl, amino, substituted amino, aminoalkyl, haloalkyl, hydroxyalkyl, or sulfonyl.

In some further embodiments, the present invention provides compounds with the following formulae, wherein A and B are substituted with $R^1$ and $R^2$ as indicated.

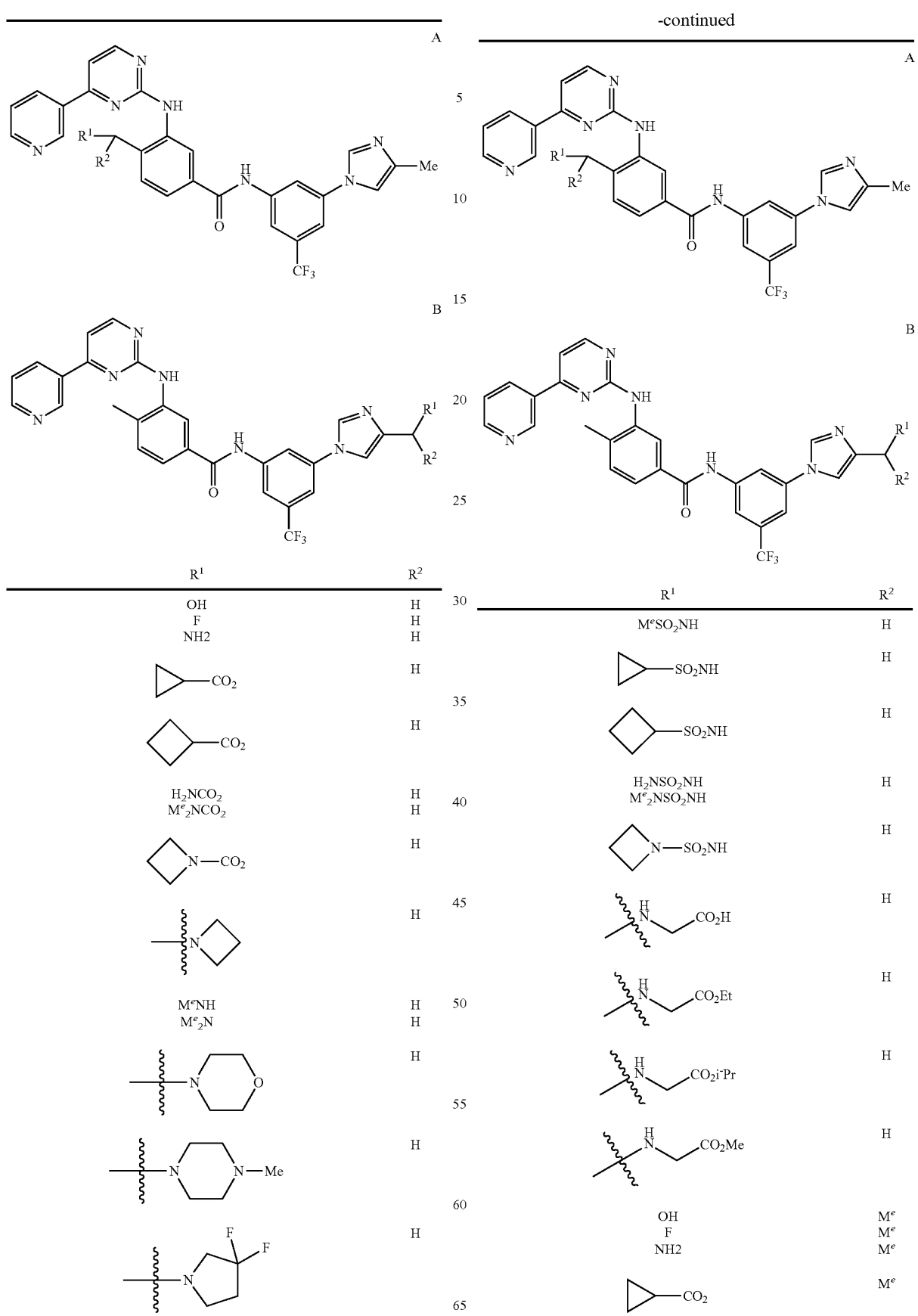

In some embodiments, the present invention provides nilotinib analogs with improved properties, such as improved efficacy, pharmacokinetics, safety, and/or specificity. In some embodiments, the present invention provides nilotinib analogs that provide therapeutic benefits. In particular, in some embodiments, the present invention provides nilotinib analogs that provide increased inhibition of Abl, reduced clearance, longer half lives, favorable distribution in vivo, and/or improved bioavailability. In some additional embodiments, the present invention provides nilotinib analogs with improved safety factors (e.g., no interaction with undesirable targets, such as hERG, liver CYPS, etc.), differentiated kinase specificity, etc. In some further embodiments, the present invention provides nilotinib analogs with improved efficacy and safety relative to nilotinib.

Historically, pharmaceutical companies have been challenged to maintain their drug pipelines, particularly in view of the pressure placed on drug discovery and development for environmentally-friendly methods and compositions, increasing cost-constraints on healthcare systems, and demanding regulatory requirements. Thus, there remains a need in the art for cost-effective, sustainable methods for the discovery and development of new and/or improved drugs (See e.g., Paul et al., Nat. Rev. Drug Disc., 9:203-214 [2010]). Indeed, innovation in synthetic methods has the ability to drive the expansion of drug pipelines (e.g., palladium catalyzed reaction). Late stage functionalization of completed drug candidate scaffolds has been investigated for the generation of chemical diversity. Fluorination and oxidation are two transformations that have found the most use.

In contrast to currently used methods, the present invention provides methods and compositions utilizing enzymes for the synthesis and development of new drug candidates. Enzymes provide the means to generate great structural diversity, facilitating investigations into the efficacy and safety of compounds of potential interest. These methods are environmentally friendly, sustainable, and cost-effective.

During the development of the present invention, a specific isoform of the cytochrome P450 monooxygenases, namely the enzyme from *Bacillus megaterium* (BM3) was used. Oxidation of a biologically active small molecule by cytochrome P450 monooxygenase BM3 or related enzymes was used to generate closely-related drug analogs, some of which have improved activity and/or diminished unfavorable characteristics relative to the parent drug. Furthermore, the addition of a hydroxyl group in some of the analogs provides a functional handle for creating addition analogs.

MCYP0035 is a cytochrome P450 monooxygenase BM3 (Codexis, Redwood City, Calif.) that oxidizes nilotinib (1), at one of the two methyl groups to give alcohol (2).

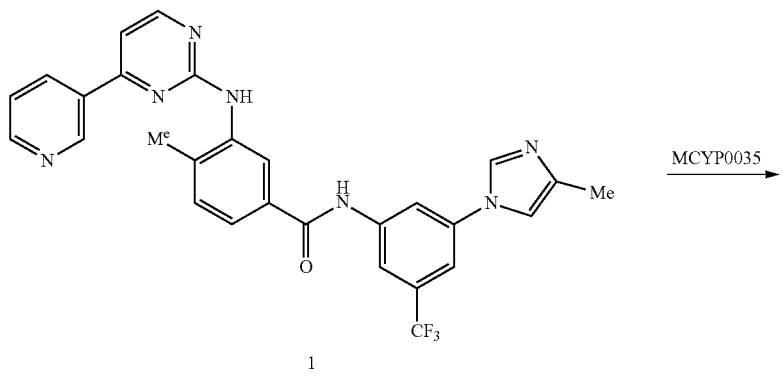

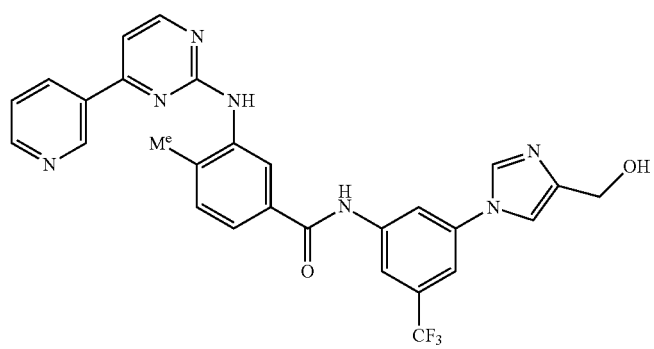

Table 1 shows the product that was generated from nilotinib (1), a Bcr/Abl inhibitor. Nilotinib was hydroxylated on the imidazole methyl group to give hydroxy-nilotinib (2). This compound was shown to have the same $IC_{50}$ (2 nM) against Abl as nilotinib. Selectivity against other kinases including cKit, cSRC, Flt1 and PDGFRα was slightly diminished.

TABLE 1

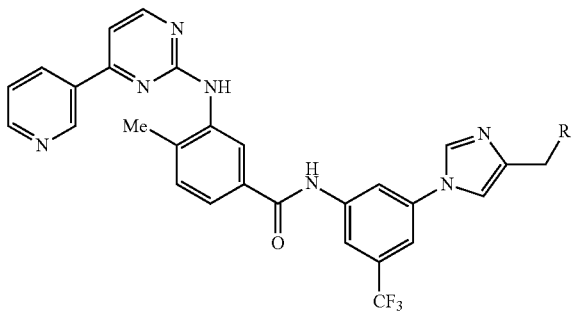

| Compd | R | Abl $IC_{50}$ | cKit $IC_{50}$ | cSRC $IC_{50}$ | Flt1 $IC_{50}$ | PDGFRα $IC_{50}$ |
|---|---|---|---|---|---|---|
| 1 | H | 2 | >10,000 | 3700 | 1300 | 3100 |
| 2 | OH | 2 | 1300 | 1300 | 1100 | 1900 |

With the structure of compound 2 known, the chemical synthesis shown in Scheme 1 was used to produce additional quantities of the compound. Commercially available fluoroaryl compound 3 was subjected to nucleophilic aromatic substitution with hydroxymethylimidazole to give intermediate 4. The nitro group was reduced with iron to give aniline 5 and the hydroxyl group protected as the TBS ether to give silylated compound 6. Compound 6 was coupled with commercially available acid 7 to give amide 8 after which the TBS protecting group was removed to provide 2. Alcohol 2 was oxidized to give aldehyde 9 which was used for the synthesis of some analogs.

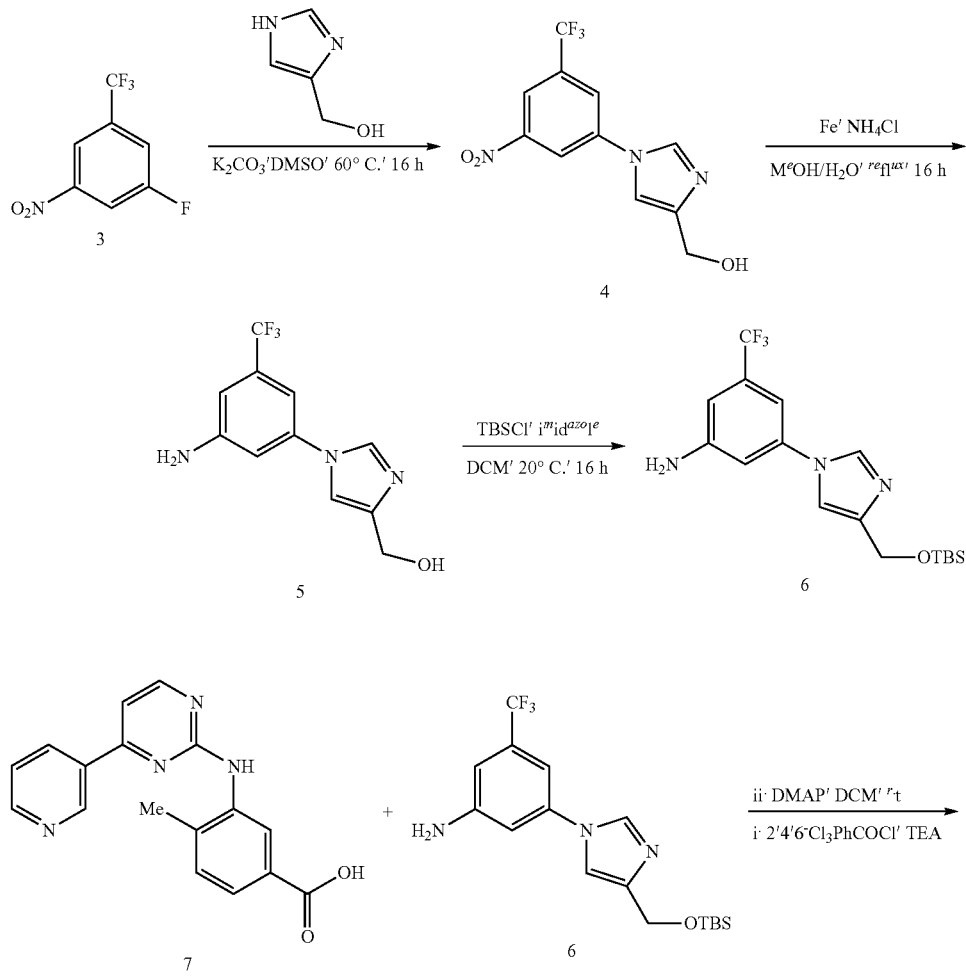

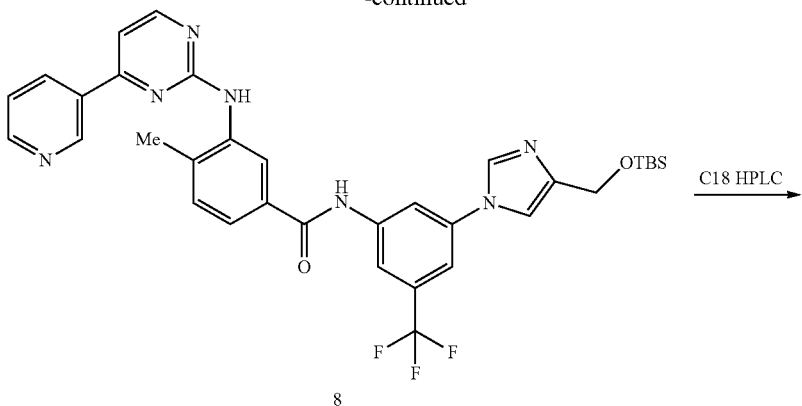

8

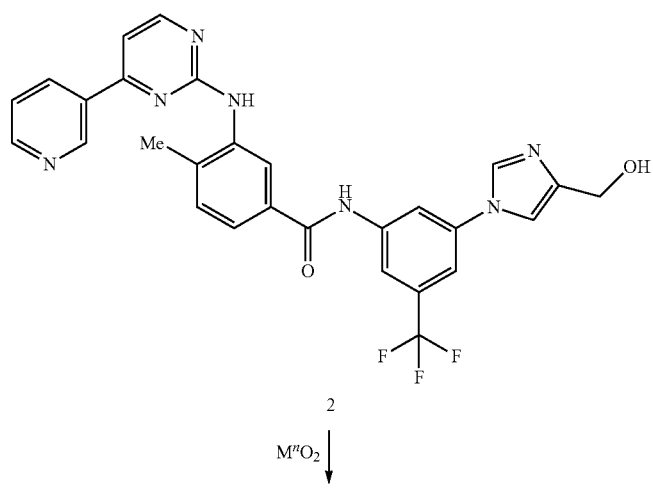

2

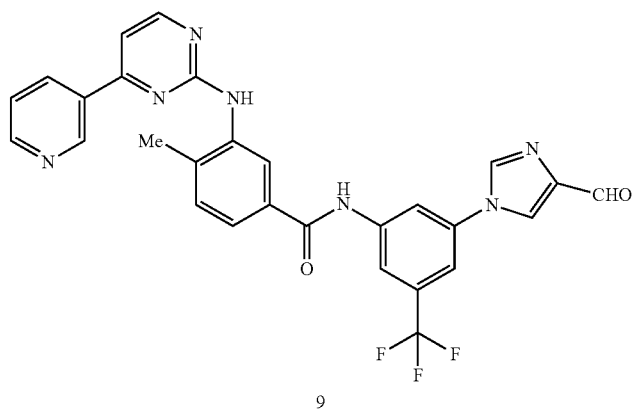

9

Analogs of nilotinib were prepared from compounds 1 or 2. Two groups of analogs were developed, the first group was produced by reacting the hydroxyl group of 2 with "capping groups" (Table 2); the second group was produced from aldehyde 9, using various nucleophiles (Table 3). The first set of analogs includes a fluoride 10, produced by deoxyfluorination with DAST; an esterase resistant cyclopropyl ester 11, produced via acylation with the acid chloride; and a carbamate 12, produced by carbamoylation with trichloroacetylisocyanate followed by hydrolysis of the resulting trichloroacetimide.

TABLE 2

[Structure of compound 2: pyridine-pyrimidine-NH-methylphenyl-C(=O)NH-phenyl(CF3)-imidazole-CH2OH] → Conditions

2

[Structure of compounds 10-12: same core with imidazole-CH2-R]

10-12

| product | Conditions | R |
|---|---|---|
| 10 | DAST, DCM, 0-20° C., 5 h | F |
| 11 | ▷—COCl, DMAP, DMF, 20° C., 5 h | ▷—CO2 |
| 12 | 1. Cl3CCONCO, DCM, 20° c., 2 h<br>2. K2CO3, MeOH, 2 h | H2NCO2 |

The nucleophiles used to produce the second set of analogs included methylmagnesium bromide and amines. Addition of methylmagnesium bromide gave the secondary alcohol as a mixture of enantiomers that was separated by supercritical fluid chiral chromatography, as known in the art, to provide the two pure enantiomers, 13 and 14. Seven amines were added in reductive amination reaction to give compounds 15-21, shown below, in Table 3. Alkylation with glycine methyl ester hydrochloride gave the amino acid methyl ester (22).

TABLE 3

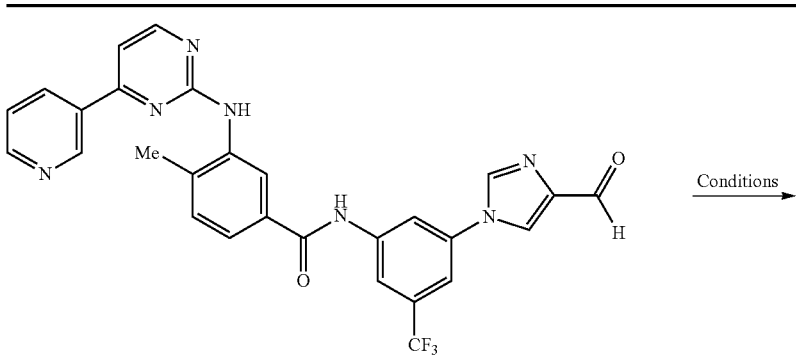

9

TABLE 3-continued

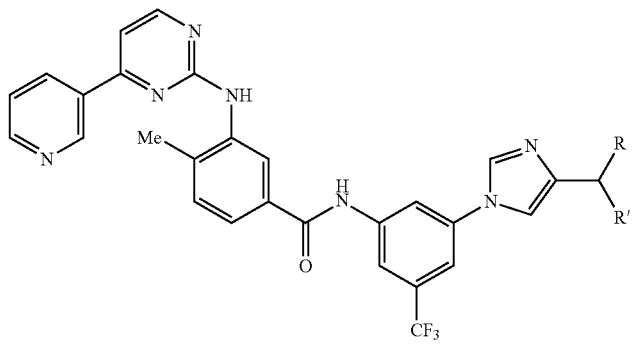

13-21

| product | Conditions | R | R' |
|---|---|---|---|
| 13 | MeMgBr, THF, 0° C., 1 h | OH (enantiomer 1) | Me |
| 14 | MeMgBr, THF, 0° C., 1 h | OH (enantiomer 2) | Me |
| 15 | ⟨azetidine⟩NH, NaCNBH$_4$, MeOH, 20° C., 4 h | N-azetidinyl | H |
| 16 | MeNH$_2$, NaCNBH$_4$, MeOH, 20° C., 4 h | MeNH | H |
| 17 | Me$_2$NH, NaCNBH$_4$, MeOH, 20° C., 4 h | Me$_2$N | H |
| 18 | Me—N⟨piperazine⟩NH, NaCNBH$_4$, MeOH, 20° C., 4 h | N-(4-methylpiperazinyl) | H |
| 19 | O⟨morpholine⟩NH, NaCNBH$_4$, MeOH, 20° C., 4 h | N-morpholinyl | H |
| 20 | 3,3-difluoropyrrolidine NH, NaCNBH$_4$, MeOH, 20° C., 4 h | N-(3,3-difluoropyrrolidinyl) | H |
| 21 | Glycine, NaCNBH$_4$, MeOH, 20° C., 4 h | N-(3,3-difluoropyrrolidinyl) | H |
| 22 | glycine methyl ester ester HCl, NaBH$_3$CN, MeOH, rt, 2 h | NH-CH$_2$-CO$_2$Me | H |

Nilotinib (1), its OH product from cytochrome P450 monooxygenase oxidation (2), and the 13 analogs prepared subsequently (10-22) were used for Abl, hERG, and K562 cancer cell line assay testing as shown in Examples 4, 5, 6, and 7.

As described herein, the present invention provides nilotinib analogs with improved properties, such as improved efficacy, pharmacokinetics, safety, and specificity. In some embodiments, the present invention provides nilotinib analogs that provide therapeutic benefits. In particular, in some embodiments, the present invention provides nilotinib analogs with provide lower clearances, longer half lives, favorable distributions, and/or improved bioavailability. In some additional embodiments, the present invention provides nilotinib analogs with improved safety factors (e.g. no interaction with undesirable targets, such as hERG, liver CYPS, etc.), differentiated kinase specificity, etc. In some embodiments, the present invention provides nilotinib analogs with improved efficacy and safety relative to nilotinib.

Pharmaceutical formulations comprising the nilotinib analogs of the present invention can be administered in the form of dosage units comprising a predetermined amount of active ingredient per dosage unit. The dosage unit depends upon the condition being treated, the method of administration and the age, weight and condition of the patient, etc., factors which are known to those of skill in the art. In some embodiments, dosage unit formulations comprise a daily dose, part-dose, or a corresponding fraction thereof of an active ingredient. It is intended that the pharmaceutical formulations comprising the nilotinib analogs of the present invention are prepared using processes generally known in the pharmaceutical arts.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); ul, uL, μL, and μl (microliter); cm (centimeters); mm (millimeters); um and μm (micrometers); sec. and " " (i.e., quote symbol) (seconds); min(s) and "'" (i.e., an apostrophe) (minute(s)); h(s) and hr(s) (hour(s)); U (units); MW (molecular weight); rpm (rotations per minute); rt (room temperature); ° C. (degrees Centigrade); MeOH (methanol); TBS (tert-butyldimethylsilyl); THF (tetrahydrofuran); TEA (triethylamine); DMAP (dimethylaminopyridine); DAST (diethylaminosulfur trifluoride); DNA (deoxyribonucleic acid); RNA (ribonucleic acid); SFC (supercritical fluid chromatography); HPLC (high pressure liquid chromatography); U and UV (ultraviolet); DMSO (dimethylsulfoxide); CRO (contract research organization); Calbiochem (Calbiochem, available from EMD Millipore Corp., Billerica, Mass.); NEB (New England Biolabs, Ipswich, Mass.); Sigma-Aldrich (Sigma-Aldrich, St. Louis, Mo.; Invitrogen (Invitrogen, Life Technologies, Grand Island, N.Y.); Life Technologies (Life Technologies, Carlsbad, Calif.); Stratagene (Stratagene, now an Agilent Technologies company); Agilent (Agilent Technologies, Inc., Santa Clara, Calif.); Molecular Devices (Molecular Devices, Sunnyvale, Calif.); USBio (US Biological, Swampscott, Mass.); Qiagen (Qiagen Inc., Germantown, Md.); Codexis (Codexis, Inc., Redwood City, Calif.); Anhui (Anhui Sanxing Resin Technology Co., Ltd. China); Merck-Milliore (Merck-Milliore; Dundee, United Kingdom); Promega (Promega, Inc., Madison, Wis.); Perkin Elmer (Perkin Elmer, Santa Clara, Calif.); Aviva BioSciences (Aviva BioSciences Corp., San Diego, Calif.); Sophion (Sophion; part of Biolin Scientific, Stockholm, Sweden); Bio-Rad (Bio-Rad Laboratories, Hercules, Calif.); ACME (ACME Bioscience, Inc., Palo Alto, Calif.); and RBC (Reaction Biology Corporation, Malvern Pa.).

Example 1

Nilotinib Biocatalytic Oxidation

MCYP Screening Procedure

Drugs and drug candidates were screened against a commercially available MCYP panel comprising a set of 96 different recombinant cytochrome P450 monooxygenases (Codexis) using the standard protocol provided with the panel. The samples were analyzed by LC/MS with a Finnigan LXQ ion trap Mass Spectrometer.

Data Analysis Procedure

LC/MS/MS chromatograms were visually inspected for the parent peak for nilotinib. Ion extraction was performed for M+1 of the parent drug and M+1+16 to identify any mono-oxidized products. The masses of any other peaks >5% in the UV chromatogram or the TIC chromatogram were noted. The data for all the 96 wells were then analyzed using the parent drug mass and any products detected during the qualitative analysis. Conversion was determined as the sum of the product peak areas divided by the total peak areas.

Scale-Up Procedure for Biocatalytic Synthesis of Compound 2

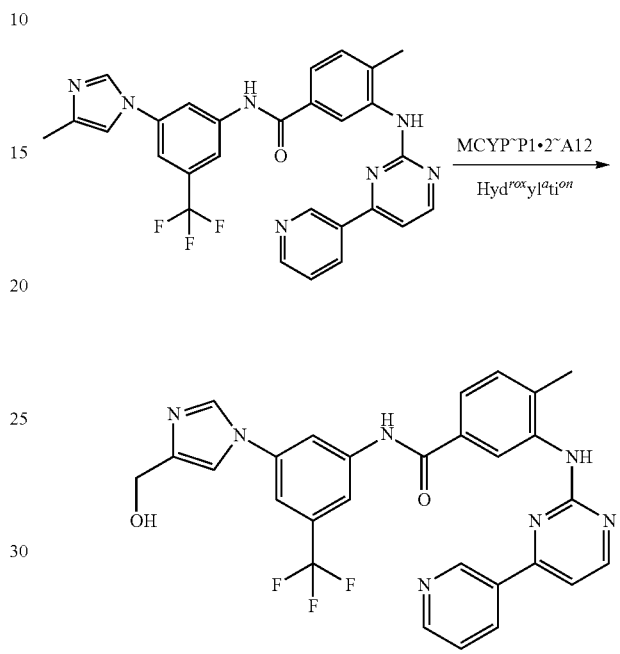

MicroCYP buffer mix (5600 mg) was dissolved in water (195 mL). Enzyme MCYP-P1.2-A12 (465 mg, 400 nmol) was added to the mix, forming a light yellow suspension. Then, Nilotinib (50.0 mg, 0.094 nmol) dissolved in DMSO (5.0 mL) was added to the above mixture. The resulting solution was shaken (110 rpm) in the incubator at 30° C., for 24 hrs. LCMS was used to detect whether the starting material was well consumed. In this case, LCMS indicated that 34% was converted to the desired product and 66% was the starting material.

The resulting solution was diluted with MeOH (100 mL), which was poured onto the D101 resin (75 g; Anhui) to remove protein and buffer components. The resin was washed with water (3 L) followed by MeOH (3 L). The MeOH eluent was collected and evaporated to afford the crude product. The residue was further purified by HPLC to give a light yellow solid as the final product (10.0 mg).

Example 2

Testing of Nilotinib (1) and Hydroxy-Nilotinib (2) with Abl, cKit, cSRC, Flt1 and PDGFRα Assays The nilotinib analogs prepared as described in Example 1 were tested for their activities on five human kinases (Abl [h]), cKit[h]), Flt1[h], and PDGFRα[h]). The assays were performed at Merck-Milliore, using their standard assay protocols

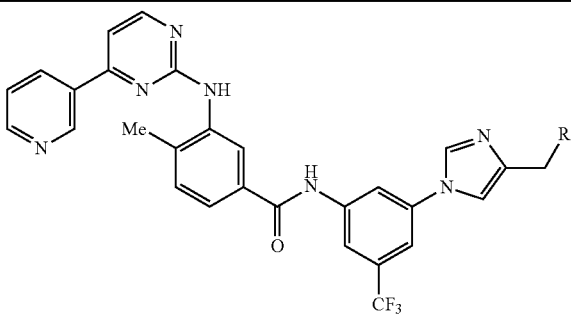
| Compd | R | Abl IC$_{50}$ | cKit IC$_{50}$ | cSRC IC$_{50}$ | Flt1 IC$_{50}$ | PDGFRα IC$_{50}$ |
|---|---|---|---|---|---|---|
| 1 | H | 2 | >10,000 | 3700 | 1300 | 3100 |
| 2 | OH | 2 | 1300 | 1300 | 1100 | 1900 |
Example 3
Chemical Synthesis of Compound 2 and Oxidation to Aldehyde 9
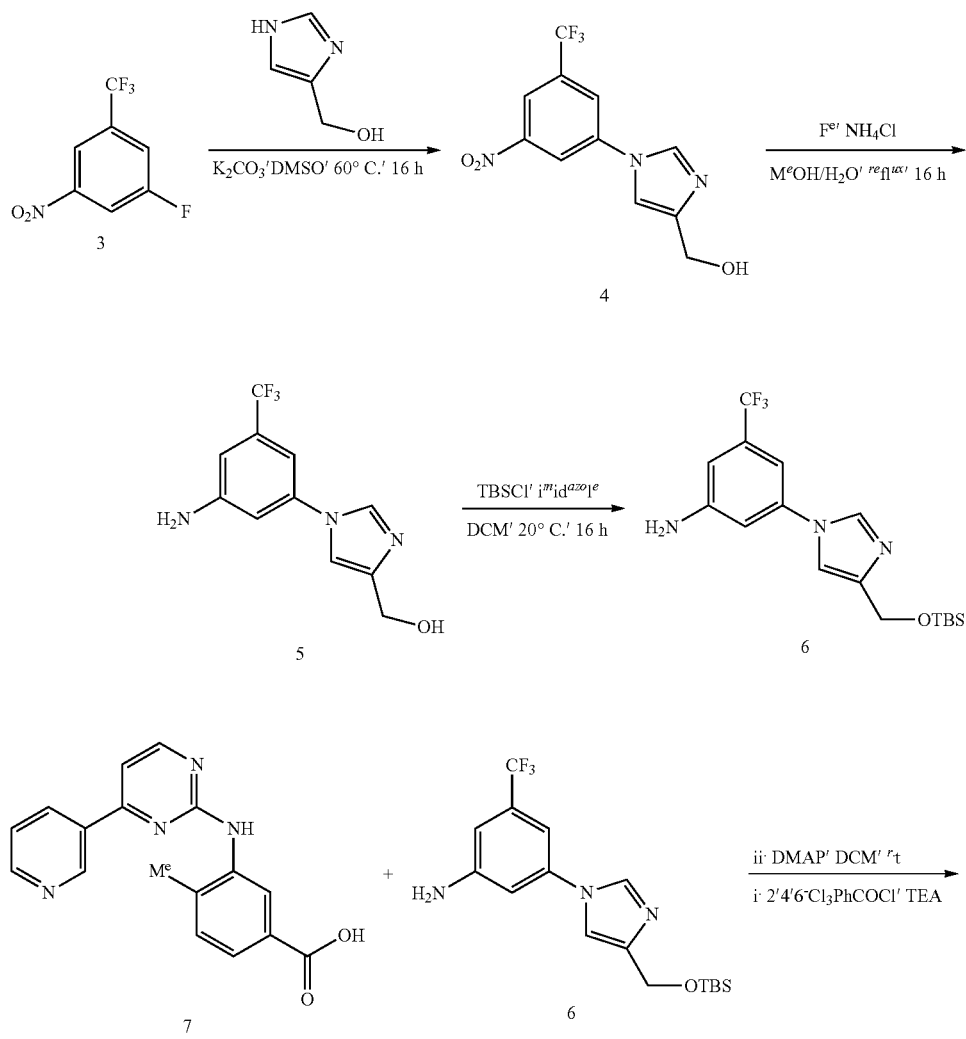

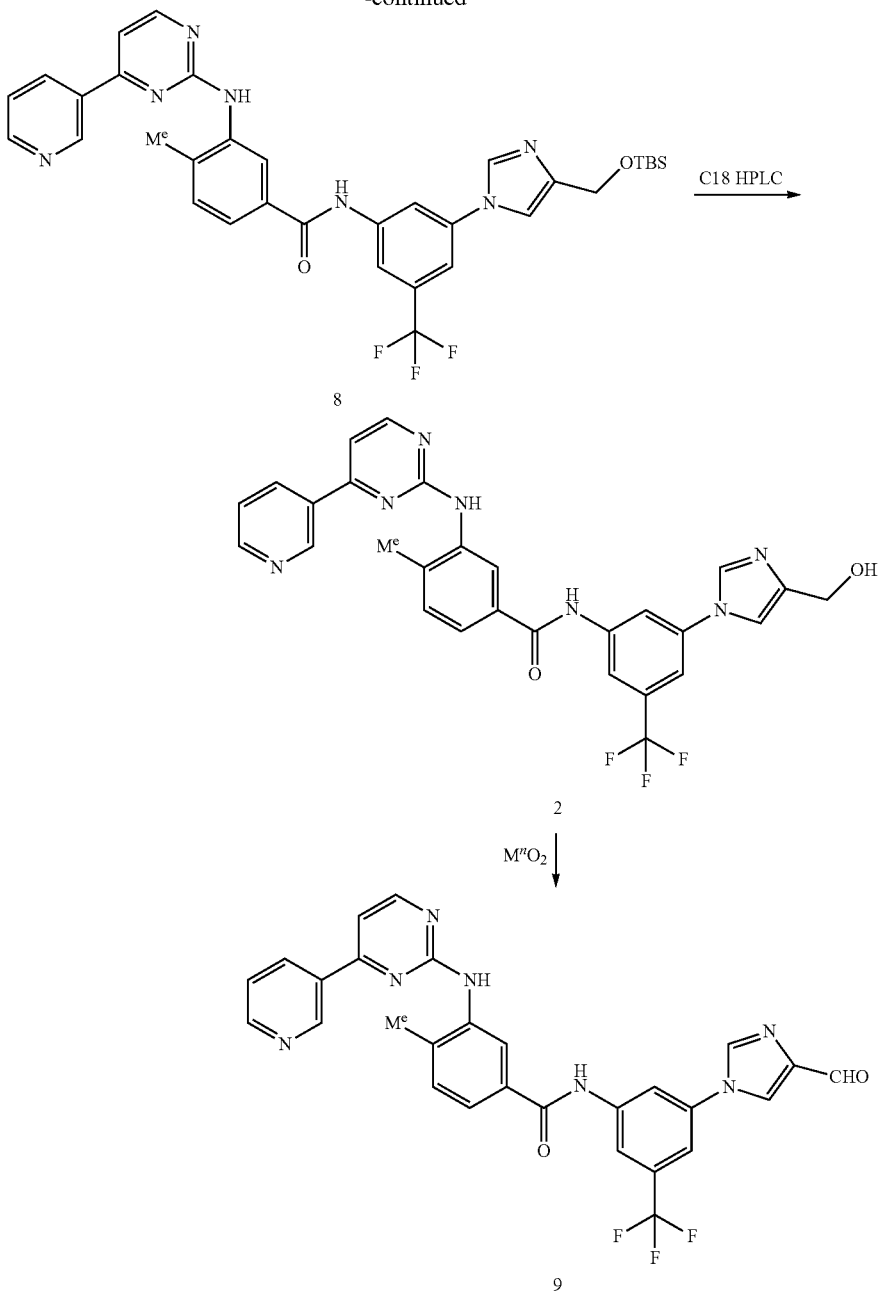

In this Example, steps in the chemical synthesis of Compound 2 are provided.

Step 1:

First, 1-fluoro-3-nitro-5-(trifluoromethyl)benzene (3, 10.0 g, 47.8 mmol, 1 equiv) and 1H-imidazol-4-ylmethanol (12.9 g, 95.7 mmol, 2 equiv) were dissolved in DMSO (60 mL). Then, $K_2CO_3$ (9.91 g, 71.7 mmol, 1.5 equiv) was added and the mixture was heated to 80° C. and stirred at this temperature for 10 hrs. The reaction was quenched with water and extracted with ethyl acetate. The organic layers were combined and evaporated to remove the solvent, further purified by column chromatography, resulting in compound 4 as a yellow solid (3.5 g)

Step 2:

First, [1-[3-nitro-5-(trifluoromethyl)phenyl]imidazol-4-yl]methanol (4, 9.5 g, 33.1 mmol, 1 equiv) was dissolved in MeOH (50 mL) and $H_2O$ (10 mL). Then, iron powder (8.65 g, 132.3 mmol, 4 equiv) and $NH_4Cl$ (7.08 g, 132 mmol, 4 equiv) were added to the mixture. The resulting reaction solution was heated to 80° C. and stirred for 10 hrs at this temperature. The reaction was cooled to room temperature and extracted with ethyl acetate. The organic layers were combined and evaporated to remove the solvent, which was further purified by column chromatography, producing compound 5 as a yellow solid (8.0 g).

Step 3:

First, [1-[3-amino-5-(trifluoromethyl)phenyl]imidazol-4-yl]methanol (5, 2.0 g, 7.8 mmol, 1. equiv) was dissolved in dichloromethane (40 mL). Then, imidazole (1.06 g, 15.6 mmol, 2 equiv) and TBSCl (2.34 g, 15.6 mmol, 2 equiv) were added to the mixture. The resulting reaction mixture was stirred at room temperature for 10 hrs. The reaction was quenched with water and extracted with dichloromethane. The organic layers were combined and evaporated to remove the solvent, which was further purified by preparative HPLC, giving compound 6 as an off white solid (1.2 g).

Steps 4&5:

First, 4-methyl-3-[[4-(3-pyridyl)pyrimidin-2-yl]amino]benzoic acid (7, 1.0 g, 3.26 mmol, 1 equiv) was dissolved in THF (30 mL). Then, TEA (661 mg, 6.53 mmol, 2 equiv) and 2,4,6-trichlorobenzoyl chloride (1.19 g, 4.90 mmol, 1.5 equiv) was added to the THF solution in this order. The mixture was stirred at room temperature for 2 hrs. Then, DMAP (598 mg, 4.90 mmol, 1.5 equiv) and 3-[4-[[tert-butyl(dimethyl)silyl]oxymethyl]imidazol-1-yl]-5-(trifluoromethyl)aniline (6, 1.46 g, 3.92 mmol, 1.2 equiv) were added to the above mixture and the reaction was stirred for another 10 hrs. The reaction was quenched with water and the product purified by preparative HPLC (C18, 10-45% acetonitrile/water, 0.075% added TFA) giving compound 8 as a white solid (700 mg). The TBS group was removed during HPLC purification when subjected to the acidic the mobile phase.

Step 6:

First, N-[3-[4-(hydroxymethyl)imidazol-1-yl]-5-(trifluoromethyl)phenyl]-4-methyl-3-[[4-(3-pyridyl)pyrimidin-2-yl]amino]benzamide (2, 350 mg, 642 umol, 1 equiv) was dissolved in acetonitrile (10 mL). Then, MnO$_2$ (223 mg, 2.57 mmol, 4 equiv) was added to the mixture. This reaction mixture was then heated to 50° C. and stirred for 16 hrs. This heated reaction mixture was filtered to remove solids. The resulting solution was evaporated to remove the solvent, giving compound 9 as a white solid (250 mg).

Example 4

Preparation of Nilotinib Derivatives (10-22)

Various nilotinib analogs were prepared using standard chemical transformation methods, as known in the art and shown below for derivatives 10-22.

Preparation of Derivative 10

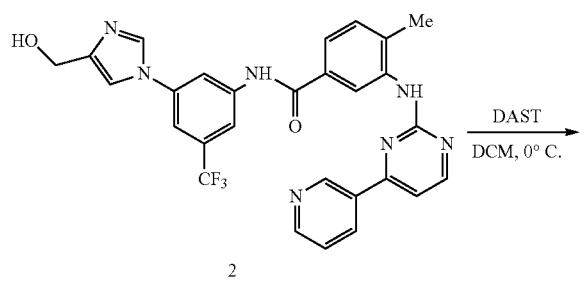

2

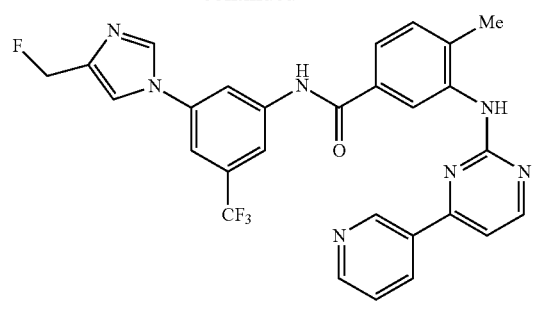

10

First, N-[3-[4-(hydroxymethyl)imidazol-1-yl]-5-(trifluoromethyl)phenyl]-4-methyl-3-[[4-(3-pyridyl)pyrimidin-2-yl]amino]benzamide (2, 60.0 mg, 110 umol, 1 equiv) was dissolved in dichloromethane (20 mL). Then, the solution was cooled to 0° C. and DAST (17.7 mg, 110 umol, 1 equiv) was added. The resulting mixture was maintained at 0° and stirred for another 1 hr. Then, the reaction was warmed to room temperature and stirred for another 4 hrs. The reaction was quenched with water and extracted with ethyl acetate. The organic layers were combined and evaporated to remove the solvent. The resulting residue was further purified by HPLC, resulting in compound 10 as a yellow solid (10 mg).

Preparation of Derivative 11

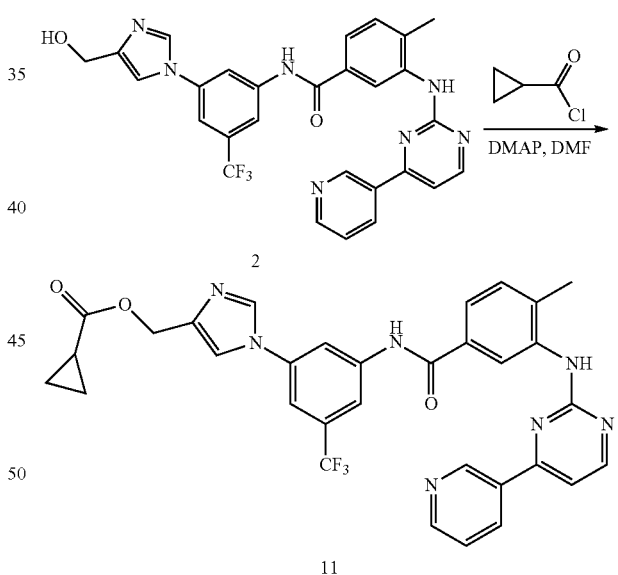

11

First, N-[3-[4-(hydroxymethyl)imidazol-1-yl]-5-(trifluoromethyl)phenyl]-4-methyl-3-[[4-(3-pyridyl)pyrimidin-2-yl]amino]benzamide (2, 60.0 mg, 110 umol, 1 equiv) was dissolved in DMF (10 mL). Then, cyclopropanecarbonyl chloride (17.16 mg, 165 umol, 1.5 equiv) was added to the mixture. The resulting reaction mixture was stirred at room temperature for 4 hrs. The reaction mixture was then quenched with water and extracted with ethyl acetate. The organic layers were combined and evaporated to remove the solvent, which was further purified by HPLC, resulting in compound 11 as a yellow solid (20.0 mg).

Preparation of Derivative 12

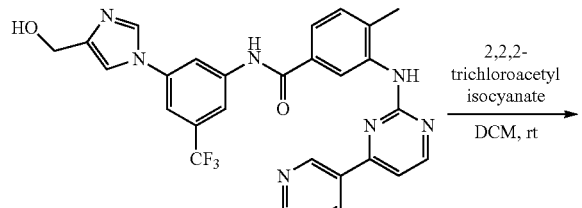

2

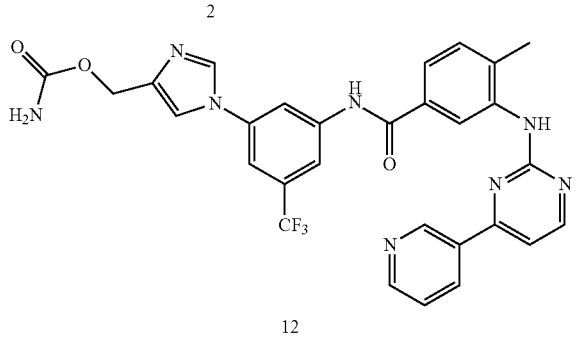

12

First, N-[3-[4-(hydroxymethyl)imidazol-1-yl]-5-(trifluoromethyl)phenyl]-4-methyl-3-[[4-(3-pyridyl)pyrimidin-2-yl]amino]benzamide (2, 60.0 mg, 110 umol, 1 equiv) was dissolved in dichloromethane (10 mL). Then, 2,2,2-trichloroacetyl isocyanate (41.44 mg, 219.98 umol, 2 equiv) was added to the mixture, which was then stirred at the room temperature for 2 hrs. Then, $K_2CO_3$ (22.8 mg, 164.98 umol, 1.50 equiv) dissolved in MeOH (10 mL) was added to the mixture. The resulting mixture was stirred for an additional 2 hrs. The reaction was quenched with water and extracted with ethyl acetate, purified by preparative HPLC, to produce compound 12 (20 mg) as the final product.

Preparation of Derivatives 13 and 14

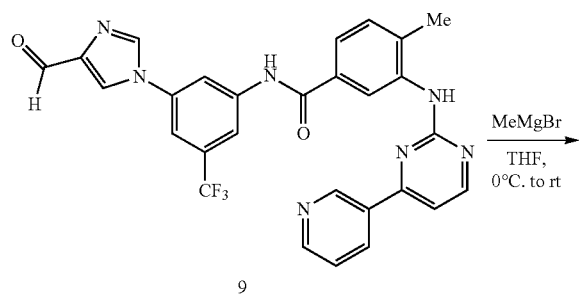

9

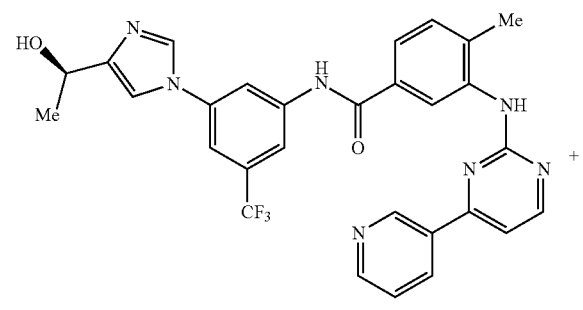

13

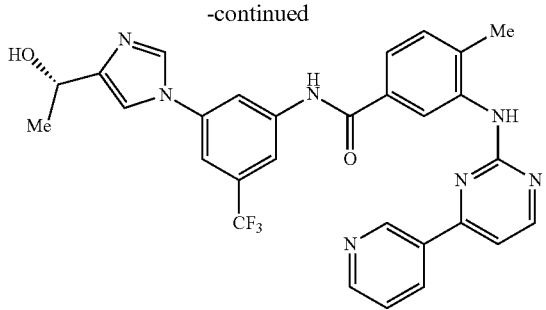

14

First, N-(3-(4-formyl-1H-imidazol-1-yl)-5-(trifluoromethyl)phenyl)-4-methyl-3-((4-(pyrimidin-3-yl)pyrimidin-2-yl)amino)benzamide (9, 250 mg, 460 umol, 1 equiv) was dissolved in THF (20 mL), cooled down to 0° C. Then, MeMgBr (3M in diethyl ether, 920 umol, 2 equiv) was added, dropwise. The reaction mixture was allowed to stir at the room temperature for 10 hr. The reaction was quenched with water and extracted with ethyl acetate, which was further purified by HPLC and SFC to produce isomers 13 and 14 white solids (10 mg) and (15 mg) separately.

Preparation of Derivatives 15-20

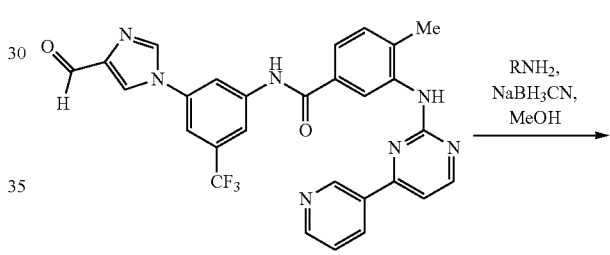

9

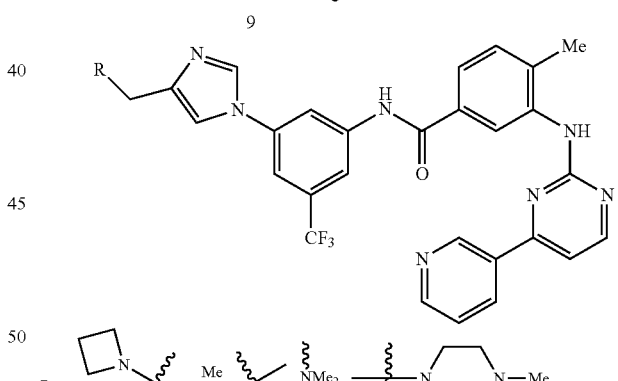

First, N-[3-[4-(hydroxymethyl)imidazol-1-yl]-5-(trifluoromethylphenyl]-4-methyl-3-[[4-(3-pyridyl)pyrimidin-2-yl]amino]benzamide (9, 60.0 mg, 110 umol, 1 equiv) was dissolved in MeOH (10 mL). Then, TMA was added to adjust pH to 6-7, then a catalytic amount of AcOH, amine (1.2 equiv) and $NaBH_3CN$ were added at 25° C. The mixture was stirred at 25° C. for 16 hrs before LC-MS showed the reaction was completed, and the crude product was purified by preparative HPLC to give Derivatives 15-20.
Preparation of Derivative 21

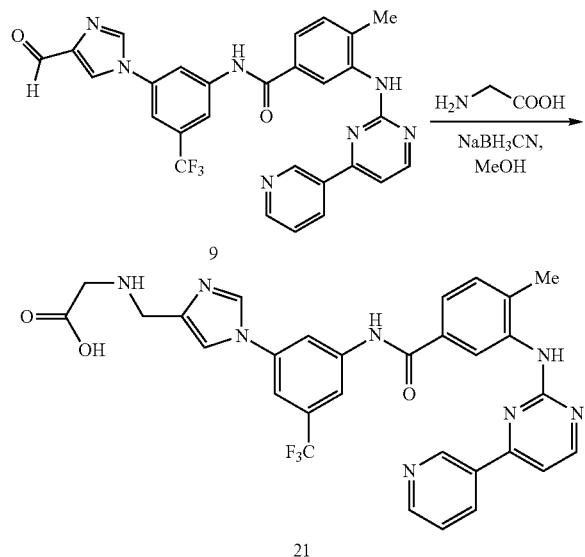

First, N-[3-[4-(hydroxymethyl)imidazol-1-yl]-5-(trifluoromethyl)phenyl]-4-methyl-3-[[4-(3-pyridyl)pyrimidin-2-yl]amino]benzamide (9, 100 mg, 184 umol, 1 equiv) was dissolved in MeOH (10 mL). Then, 2-aminoacetic acid (27.6 mg, 367 umol, 2 equiv) and NaBH₃CN (22.7 mg, 367 umol, 2 equiv) were added. The reaction was stirred at the room temperature for 2 hr. The reaction was evaporated to remove the solvent, which was further purified by HPLC to provide 21 as a yellow solid (5.0 mg).
Preparation of Derivative 22

To a solution of N-[3-[4-(hydroxymethyl)imidazol-1-yl]-5-(trifluoromethyl)phenyl]-4-methyl-3-[[4-(3-pyridyl)pyrimidin-2-yl]amino]benzamide (90 mg, 0.17 mmol, 1.0 eq) in methanol (10 mL) were added catalytic amount of AcOH, glycine methyl ester hydrochloride (25 mg, 0.20 mmol, 1.2 eq) and NaBH₃CN (17.4 mg, 0.28 mmol, 1.5 eq). The reaction mixture was stirred at rt for 2 h. The mixture was evaporated to dryness, which was further purified by pre-HPLC to give compound 22 (14 mg, 14%) as a slightly yellow solid.

Example 4

Evaluation of Nilotinib (1), Hydroxy-Nilotinib (2) and Nilotinib Analogs (10-21) in Abl and hERG Binding Assays In this Example, the testing of nilotinib, nilotinib analogs 10-21, and the hydroxy product of nilotinib are described. The nilotinib analogs prepared as described in Example 1 were tested for their inhibition of human Abl (Abl[h]) as well as hERG binding. Inhibition of Abl[h] was assessed using commercially available Z′-LYTE™ Kinase Assay kits using protocols provided by the manufacturer (LifeTechnologies).

A summary of the $IC_{50}$s for Abl[h] inhibition for nilotinib (1), hydroxy-nilotinib (2) and 12 analogs is shown in Table 4 and in FIG. 1.

TABLE 4

| $IC_{50}$ Values ABL $IC_{50}$ | |
|---|---|
| Compound | IC50 (nM)* |
| 1 | + |
| 2 | ++ |

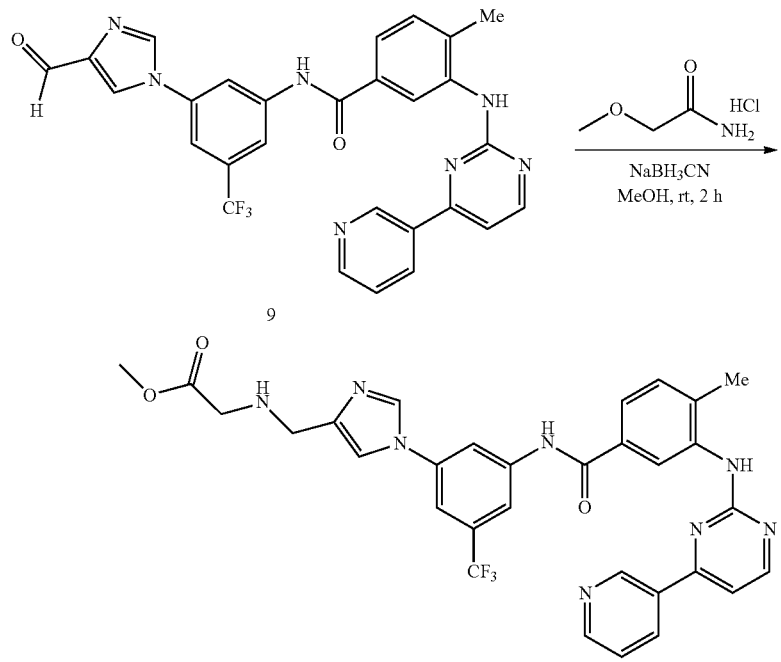

TABLE 4-continued

IC$_{50}$ Values
ABL IC$_{50}$

| Compound | IC50 (nM)* |
|---|---|
| 10 | – |
| 11 | – |
| 12 | – |
| 13 | + |
| 14 | ++ |
| 15 | +++ |
| 16 | +++ |
| 17 | +++ |
| 18 | +++ |
| 19 | +++ |
| 20 | – |
| 21 | +++ |

*"+": IC50 is similar to nilotinib; "–": IC50 is >20% higher than nilotinib; "++": IC50 is <50% of nilotinib; "+++": IC50 is <15% of nilotinib hERG Binding Assay:

CHO cells stably expressing hERG potassium channels obtained from Aviva BioSciences were used for this test. The cells were cultured in a humidified and air-controlled (5% $CO_2$) incubator at 37° C. and were used at more than 75% confluency in the experiments.

Test compounds and the positive control, Amitriptyline, were dissolved in 100% DMSO to obtain 333× stock solutions for different test concentrations. Then, the stock solutions were further diluted (1:333) into the extracellular solution obtained from the cell cultures, to achieve the final concentrations used for testing. Visual check for precipitation was conducted before testing. The final DMSO concentration in the extracellular solution was 0.30% for the test compounds and Amitriptyline (positive) control.

The hERG QPatchHTX assay was conducted at room temperature. The whole-cell protocols, voltage protocols and application protocols were established with QPatch Assay Software 5.0 (Sophion).

The IC50s of the test compounds on whole cell hERG currents are summarized in Table 5 below.

TABLE 5

IC$_{50}$ Values

| Compound | IC$_{50}$ (μM)* |
|---|---|
| Amitriptyline | + |
| 15 | +++ |
| 17 | ++ |
| 18 | +++ |
| 14 | +++ |
| 21 | +++ |
| 19 | ++ |
| 16 | +++ |
| 2 | + |
| 13 | +++ |
| 1 | – |

*"+": hERG inhibition similar to amitriptyline; "–": >50% reduction in IC50 compared to amitriptyline; "++": >50% increase in IC50 compared to amitriptyline; "+++": >200% reduction in IC50 compared to amitriptyline Nilotinib, —OH derivative (6) and 8 analogs (11, 12, 13, 14, 15, 16, 17, and 19) exhibited higher potency in the Abl assay and were less inhibiting to hERG than Nilotinib (5).

Example 5

Testing of Nilotinib (1), Hydroxy-Nilotinib (2) and 8 Analogs in a K562 Cancer Cell Line Assay In this Example, Compounds 1 (Nilotinib), 2, 11, 12, 13, 14, 15, 16, 17, 18, and 19, pre-diluted in dimethyl sulfoxide (DMSO) to 10 mM were tested. Prior to use, all of the compounds were stored at −20° C. The cell line K-562 (ATCC) was used in these experiments. The cell line was maintained in liquid nitrogen until ready for use. The cell line was prepared by thawing a 1 mL vial of cells and splitting them into 2 T-75 flasks with 20 mL of RPMI 1640 medium containing L-glutamine, 4.5 g/L glucose, 1 mM sodium pyruvate, 10% fetal bovine serum, and 100 IU/mL of penicillin-streptomycin solution. After 2 days of incubation at 37° C. with 5% $CO_2$, the liquid suspension was transferred into larger flasks and fresh media were added to a total of 40 mL. To split the cells, half of the liquid suspension was aspirated and fresh media was added to the flask. Cells were split one day prior to usage.

In the assay, the test compounds were diluted into media to achieve 100 μL of 0.2 mM of each test compound. Two-fold serial dilutions were performed into 22 wells (the last well was a blank control). The K-562 cells were counted using trypan blue and a hemocytometer. Then, 100 μL of $5.0×10^4$ cells/mL were added to each well of the 96-well microtiter plate with the diluted test compounds and mixed well on a mini orbital shaker at about 150 rpm for 2 minutes. The treated plates were incubated at 37° C. with 5% $CO_2$ for 72 hours. After each incubation period, the cell viability was determined using the kit CellTiter 96® Aqueous One Solution Cell Proliferation Assay (Promega). The optical density (OD) was read using SpectraMax M5 Microplate Reader at 490 nm. The 50% inhibitory concentration ($IC_{50}$) was calculated by plotting OD versus log of the compound concentration (mM) in GraphPad Prism 4 (GraphPad) using the sigmoidal dose-response equation. All experiments were performed in duplicate.

Figure 2:
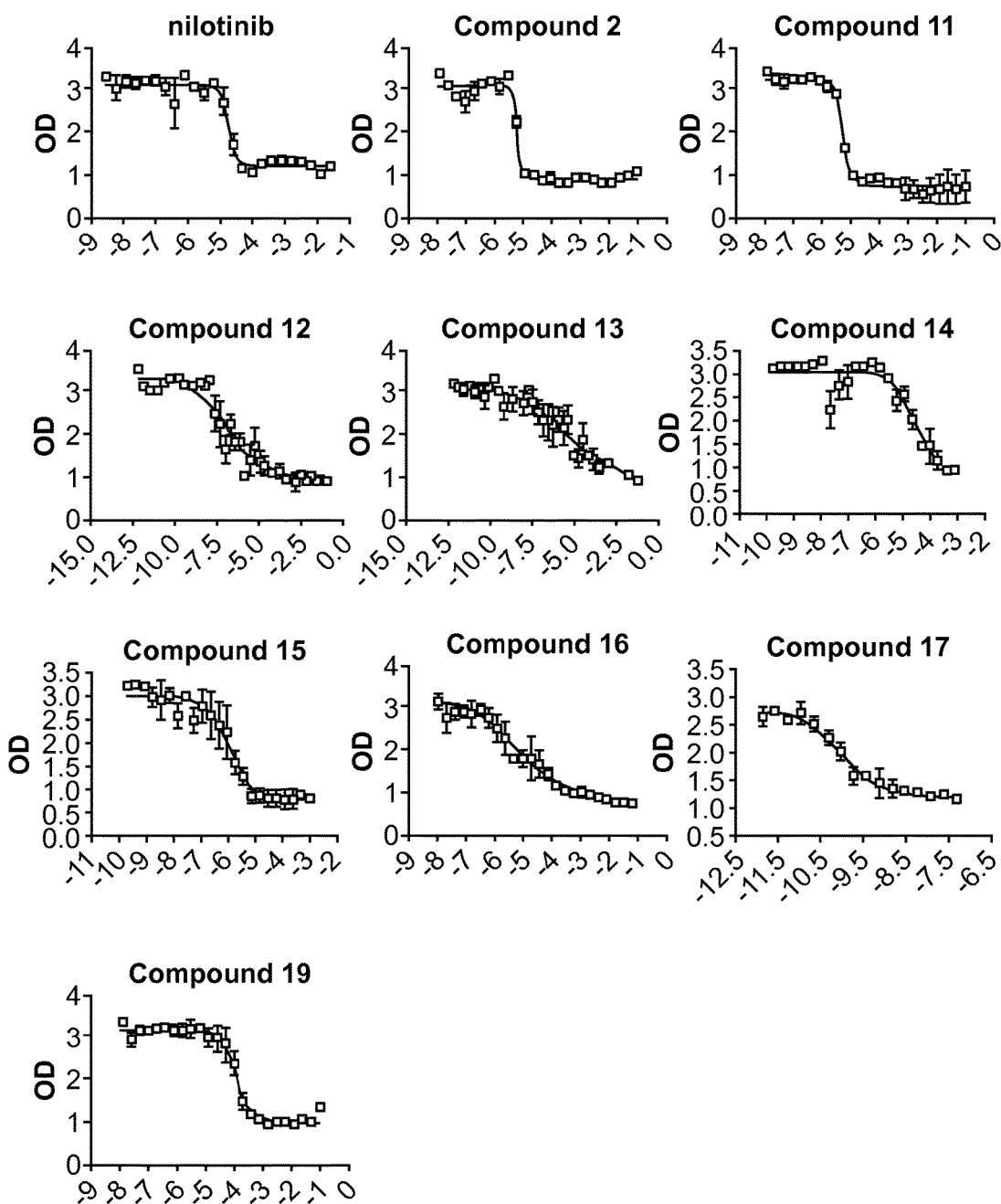

The cytotoxicity data are provided in Table 7 and FIG. 2. Only two test compounds were shown to have higher $IC_{50}$s than nilotinib when tested in the present K-562 assay (i.e., Compounds 14 and 19), indicating that these compounds are not as strongly inhibiting as nilotinib (Table 1). The rest of the test articles were found to be more inhibitory than nilotinib, with Compounds 12, 15 and 17 showing $IC_{50}$s below than 1 nM.

TABLE 7

IC$_{50}$s of Test Compounds in K-562 Assay System

| Test Compound | K-562 IC$_{50}$* |
|---|---|
| Compound 1 (nilotinib) | + |
| Compound 2 | ++ |
| Compound 11 | ++ |
| Compound 12 | +++ |
| Compound 13 | ++ |
| Compound 14 | – |
| Compound 15 | +++ |
| Compound 16 | ++ |
| Compound 17 | +++ |
| Compound 19 | – |

*"+": IC$_{50}$ similar to nilotinib; "–": IC$_{50}$ more than 25% great than IC$_{50}$ for nilotinib; "++": IC$_{50}$ more than 25% smaller than IC$_{50}$ for nilotinib; "+++": IC$_{50}$ more than 75% great than IC$_{50}$ for nilotinib.

Example 6

Evaluation of Nilotinib (1) and Nilotinib Analogs (13, 14, 17, 19, 21, and 22) in Abl Binding Assays Using a Secondary CRO In this Example, the testing methods used with nilotinib and nilotinib analogs (13, 14, 17, 19, and 21) are described.

The nilotinib analogs prepared as described in Example 1 were tested for their inhibition of human Abl (Abl[h]) binding. The synthesis and biochemical testing of these compounds was completed using alternate CROs for characterizing compounds.

Assay Protocols

Kinase assays were performed at RBC using standard protocols known to those skilled in the art. In brief, kinase, any required cofactors, substrate in DMSO, and kinase reaction mixture (by acoustic technology; Echo550; nanoliter range) were incubated for 20 minutes at room temperature. 33P-ATP was added to initiate the reaction, which was incubated for 2 hours at room temperature. Kinase activity was detected by filter-binding method.

Assay Results

As shown in Table 8, three of the five compounds tested (14, 17, and 21) inhibited Abl with better potency than lapatinib.

TABLE 8

| $IC_{50}$ Values ABL $IC_{50}$ | |
|---|---|
| Compound | IC50 (nM)* |
| 1 | + |
| 14 | ++ |
| 17 | ++ |
| 19 | + |
| 21 | ++ |
| 22 | + |

*"+": IC50 is similar to nilotinib; "−": IC50 is >20% higher than nilotinib; "++": IC50 is <50% of nilotinib; "+++": IC50 is <15% of nilotinib Example 7

Testing of Nilotinib (1) and 5 Analogs in a K562 Cancer Cell Line Assay

In this Example, experiments conducted at RBC to assess the cytotoxicity of nilotinib and compounds 14, 17, 19, 21, and 22 (i.e., test compounds) are described. All of the test compounds were kept between 4° C. to 8° C. in solid form or as solution in DMSO.

The cell line K562 was obtained from the ATCC. Test compounds were dissolved in DMSO (1 mM stock). Cell Titer-Glo® 2.0 Luminescent cell viability assay reagent was obtained from Promega. K562 lymphoblast cell line was cultured in Iscove's Modified Dulbecco's medium supplemented with 10% FBS. 100 µg/ml penicillin and 100 µg/ml streptomycin were added to all culture media. Cultures were maintained at 37° C. in a humidified atmosphere of 5% $CO_2$ and 95% air. Test compounds in DMSO were added in a source plate. 25 nL of test compounds was delivered from the source plate to each well of the 384-well cell culture plates by Echo 550. 25 µl of culture medium containing 1000 cells for each cell line was added to the wells of the cell culture plates. Cells were incubated with test compounds at 37° C., 5% $CO_2$ for 72 hours. 25 µl of Cell Titer Glo 2.0 reagent was added to each well. The contents were mixed on an orbital shaker for 2 minutes and incubated at room temperature for 10 minutes to stabilize luminescent signal. Luminescence was recorded by Envision 2104 Multilabel Reader (PerkinElmer). The number of viable cells in culture was determined based on quantization of the ATP present in each culture well. The $IC_{50}$ values were calculated and the $IC_{50}$ curves were plotted using the GraphPad Prism 4 program based on a sigmoidal dose-response equation.

The cytotoxicity data are provided in Table 9. Four test compounds were shown to have higher $IC_{50}$s than nilotinib when tested in the present K-562 assay (i.e., Compounds 17, 19, 21, and 22), indicating that these compounds are not as strongly inhibiting as nilotinib (Table 9). Compound 14 was found to be more inhibitory than nilotinib.

TABLE 9

| $IC_{50}$s of Test Compounds in K-562 Assay System | |
|---|---|
| Test Compound | K-562 $IC_{50}$* (RBC) |
| Compound 1 (nilotinib) | + |
| Compound 14 | ++ |
| Compound 17 | − |
| Compound 19 | − |
| Compound 21 | − |
| Compound 22 | − |

*"+": $IC_{50}$ similar to nilotinib; "−": $IC_{50}$ more than 25% great than $IC_{50}$ for nilotinib; "++": $IC_{50}$ more than 25% smaller than $IC_{50}$ for nilotinib: "+++": $IC_{50}$ more than 75% great than $IC_{50}$ for nilotinib.

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of the present invention.

We claim:
1. A composition comprising the compound of Formula I, wherein $R^1$ is an hydroxyl, and $R^2$, is an alkyl, each optionally substituted, or a salt thereof.

2. The composition of claim 1, wherein said composition is suitable for administration to an animal.

3. The composition of claim 2, wherein said animal is a human.

* * * * *